(12) United States Patent
Bohner et al.

(10) Patent No.: US 8,805,859 B2
(45) Date of Patent: Aug. 12, 2014

(54) METHODS AND SYSTEMS FOR RECEIVING, MAPPING AND STRUCTURING DATA FROM DISPARATE SYSTEMS IN A HEALTHCARE ENVIRONMENT

(75) Inventors: Wendy Lynne Bohner, Barrington, IL (US); David Phillip Murawski, Barrington, IL (US); Arpita Patadia, Barrington, IL (US); Rajakumari Pavuluri, Barrington, IL (US)

(73) Assignee: General Electric Company, Schenectady, NY (US)

( * ) Notice: Subject to any disclaimer, the term of this patent is extended or adjusted under 35 U.S.C. 154(b) by 43 days.

(21) Appl. No.: 13/171,183

(22) Filed: Jun. 28, 2011

(65) Prior Publication Data

US 2012/0215799 A1    Aug. 23, 2012

Related U.S. Application Data

(60) Provisional application No. 61/444,940, filed on Feb. 21, 2011.

(51) Int. Cl.
*G06F 17/30* (2006.01)
*G06F 19/00* (2011.01)

(52) U.S. Cl.
CPC .................................. *G06F 19/322* (2013.01)
USPC ......................................................... 707/755

(58) Field of Classification Search
None
See application file for complete search history.

(56) References Cited

U.S. PATENT DOCUMENTS

| | | | |
|---|---|---|---|
| 7,398,512 B2 * | 7/2008 | Martin et al. | 717/105 |
| 7,849,049 B2 * | 12/2010 | Langseth et al. | 707/602 |
| 2007/0118399 A1 * | 5/2007 | Avinash et al. | 705/2 |
| 2007/0288508 A1 * | 12/2007 | Brunswig et al. | 707/103 R |
| 2008/0046292 A1 | 2/2008 | Myers et al. | |
| 2008/0140602 A1 * | 6/2008 | Roth et al. | 706/59 |
| 2008/0208624 A1 * | 8/2008 | Morita et al. | 705/2 |
| 2008/0222121 A1 * | 9/2008 | Wiessler et al. | 707/4 |
| 2009/0089080 A1 * | 4/2009 | Meisel | 705/2 |
| 2009/0281836 A1 * | 11/2009 | Velarde | 705/3 |
| 2010/0094658 A1 * | 4/2010 | Mok et al. | 705/3 |
| 2010/0127981 A1 * | 5/2010 | Brandt et al. | 345/163 |
| 2010/0235378 A1 * | 9/2010 | Armstrong et al. | 707/769 |
| 2011/0022412 A1 * | 1/2011 | Jackson et al. | 705/3 |
| 2011/0105854 A1 | 5/2011 | Kiani et al. | |
| 2011/0119088 A1 * | 5/2011 | Gunn | 705/3 |
| 2011/0197119 A1 * | 8/2011 | Ye et al. | 715/226 |
| 2011/0202555 A1 * | 8/2011 | Cordover et al. | 707/769 |
| 2011/0225176 A1 * | 9/2011 | Siegel et al. | 707/756 |
| 2012/0215860 A1 | 8/2012 | Bohner et al. | |

OTHER PUBLICATIONS

"Supporting non HL7 message formats," retrieved from http://www.mirthcorp.com/community/forums/archive/index.php/t-239.html on Jun. 28, 2011, 2 pages.

(Continued)

*Primary Examiner* — Richard Bowen
(74) *Attorney, Agent, or Firm* — Hanley, Flight & Zimmerman, LLC

(57) ABSTRACT

Methods and systems for receiving, mapping and structuring data from disparate systems in a healthcare environment are described. An example system for processing healthcare data includes an interface to receive input and display output, the input comprising a plurality of differently formatted healthcare messages and an identifier to identify a message type of the plurality of healthcare messages received. The example system also includes a mapper to map data of the plurality of healthcare messages to respective models based on the message type identified and a data store to store the models and corresponding mapped data.

30 Claims, 17 Drawing Sheets

(56) References Cited

OTHER PUBLICATIONS

Ciccarese et al., "A Framework for Temporal Data Processing and Abstractions," AMIA 2006 Symposium Proceedings, retrieved from http://www.ncbi.nlm.gov/pmc/articles/PMC1839476/ on Jun. 28, 2011, pp. 146-150.

Nayak et al., "XML schema clustering with semantic and hierarchical similarity measures," Abstract, vol. 20, Issue 4, May 2007, retrieved from http://www.sciencedirect.com/science/article/pii/S095070510600150X on Aug. 18, 2011, 2 pages.

United States Patent and Trademark Office, "Non-Final Office Action," issued in connection with U.S. Appl. No. 13/171,191, mailed on Feb. 1, 2013, 27 pages.

Huff et al., "Development of the Logical Observation Identifier Names and Codes (LOINC) Vocabulary," Journal of the American Medical Informatics Association, vol. 5, No. 3, pp. 276-292 (1998).

Huff et al., "Linking a Medical Vocabulary to a Clinical Data Model Using Abstract Syntax Notation 1," Methods of Informatics in Medicine 37(4-5), pp. 440-452 (Nov. 1998) (17 pages).

Stephane Meystre and Peter J. Haug, "Medical Problem and Document Model for Natural Language Understanding," American Medical Informatics Association 2003 Symposium Proceedings, pp. 455-459 (2003).

Alan L. Rector, "The Interface between Information, Terminology, and Inference Models," Studies in Health Technology and Informatics 1, pp. 246-250 (2001).

A.L. Rector, W.A. Nowlan, S. Kay, C.A. Goble and T.J. Howkins, "A Framework for Modelling the Electronic Medical Record," Methods of Information in Medicine 32(2), pp. 109-119 (Apr. 1993) (21 pages).

Roberto A. Rocha, Stanley M. Huff, "Using Digrams to Map Controlled Medical Vocabularies," Proceedings of the Annual Symposium on Computer Application in Medical Care, pp. 172-176 (1994).

\* cited by examiner

METHODS AND SYSTEMS FOR RECEIVING, MAPPING AND STRUCTURING DATA FROM DISPARATE SYSTEMS IN A HEALTHCARE ENVIRONMENT

RELATED APPLICATION

This patent claims priority to U.S. Provisional Application No. 61/444,940 filed Feb. 21, 2011, which is hereby incorporated herein by reference in its entirety.

BACKGROUND

Healthcare environments, such as hospitals and clinics, typically include information systems (e.g., electronic medical record (EMR) systems, lab information systems, outpatient and inpatient systems, hospital information systems (HIS), radiology information systems (RIS), storage systems, picture archiving and communication systems (PACS), etc.) to manage clinical information such as, for example, patient medical histories, imaging data, test results, diagnosis information, management information, financial information and/or scheduling information. Different healthcare entities may differently format and/or structure healthcare documentation generated, received, transmitted and/or processed in connection therewith.

Figure 1:
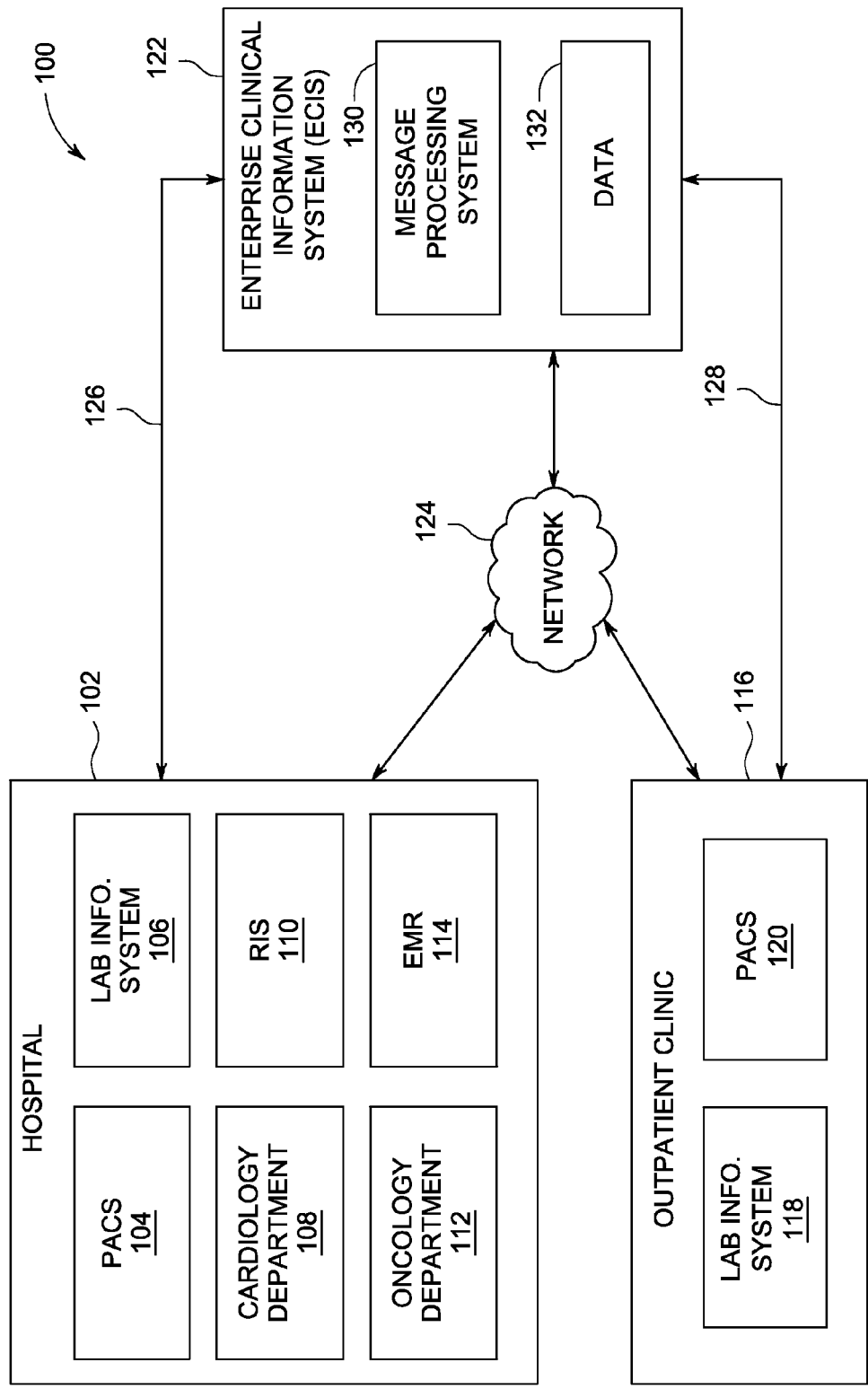
FIG. 1 is a block diagram of an example healthcare environment.

The foregoing summary, as well as the following detailed description of certain examples, will be better understood when read in conjunction with the appended drawings. For the purpose of illustrating the examples described herein, certain examples are shown in the drawings. It should be understood, however, that the present disclosure is not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems, and/or articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

When any of the appended claims are read to cover a purely software and/or firmware implementation, at least one of the elements in at least one example is hereby expressly defined to include a tangible medium such as a memory, DVD, CD, Blu-ray, etc., storing the software and/or firmware.

Examples described herein enable data from disparate clinical systems of a healthcare organization to be centralized into, for example, one central location accessible by clinicians. Thus, using the examples described, a clinician accessing data for a particular patient, may access all of the patient's relevant data and may choose, using end-user components, which of that data they would like to view. The examples described herein enable the interoperability of disparate clinical systems (e.g., existing applications and products) by aggregating associated data from these systems into standardized and/or structured formats or models prior to its storage in a data base (e.g., Clinical Data Repository). In some examples, the formats and/or models may be in an XML format. Additionally, the examples described herein enable data, once received, to be displayed using a customizable dashboard user interface. The data may include Electronic Medical Records (EMRs), data associated with IT solutions, etc.

In some examples, the dashboard user interface may include alerts and/or notifications to notify clinicians when data received varies from defined clinical standards. As the data is received from the disparate clinical systems, the data may be normalized by mapping to enable the data to be translated and stored in a structured format or model useable by other clinical systems and/or applications. As data is received from the disparate clinical systems, the vocabulary within the data may be standardized (e.g., standard Health Level Seven (HL7) language) to enable the data to be useable by other clinical systems and/or applications in clinical decision support, for example. Because of the open architecture of the example platforms described herein, customers using the examples described may leverage these platforms to build their own applications, use the platform along with other provided applications and/or customize the dashboard user interface based on the customer's specific preferences and/or needs.

Examples described herein accommodate differently formatted messages within a single universal schema enabling different devices to be connected and/or different communications to be routed between information systems. More particularly, the example systems and methods described herein enable the aggregation of fields associated with different versions of message structures such as Health Level Seven (HL7) Admit Discharge Transfer (ADT), Observation Results (ORU), Medical Document Management (MDM), etc., various 2.x HL7 versions of ADT, ORU, MDM, etc., and triggers (e.g., A01, A02, etc.). In some examples, an example universal schema definition may receive messages created by a first program in a first HL7 format while also receiving messages created by a second program in a second HL7 format by not restricting fields generated in connection with either of the formats even though those fields may not be supported across all versions or HL7 structures. In some examples, an example universal schema definition may not require fields not generated in connection with either of the first HL7 format or the second HL7 format if those fields are not supported across all versions or HL7 structures.

In contrast to known approaches, the examples described herein may provide a single universal schema definition for all triggers of each of the different HL7 message types (e.g., ADT, ORU, MDM) reducing a number of interface end points used in connection with each of the different HL7 message types of existing systems. Thus, using the examples described herein, the time and labor intensity of maintaining such systems may be reduced and simplified.

After messages having different formats are received by the universal schema, the messages may be formatted, organized and/or stored based on the message type received using the same or similar business logic. For example, based on the message and/or content received, the example system may search for different types of data within the message and set up a configuration file(s) including one or more fields of one or objects. The configuration file created may be associated with a trigger of the message received and the objects may be correlated once created. The identified data may then be conveyed to the fields and/or objects to be stored in a structured format. By searching the incoming messages to identify data to populate the fields and/or objects, the incoming message may be effectively filtered for the data desired. In some examples, a customer may customize how the messages and/or content received are processed. For example, customers may change the actions taken and/or objects created if a particular message type is received. The storage data structures may be dynamically defined at run time using a schema defined at run time, for example. The business logic may be dynamically defined at run time, for example.

After the messages having the different formats are received by the universal schema, the messages may be mapped to different fields of different objects and stored in a data structure based on the message type received and settings of a configuration user interface. In some examples, the data received may be mapped to the different fields in more than one object using the same or similar business logic regardless of the format of the message received.

Customers using the examples described herein may configure, be exposed to and/or dictate, using the configuration user interface, how messages, object states, etc., behave, are manipulated or changed as the messages are processed, specific objects are acted on, etc., to tailor the systems and methods to the customer's particular preferences. The examples described herein may be tailored such that for a first customer, a message creates new objects for saving the data. The examples described herein may be tailored such that for a second customer receiving the same message, a specific object is available that updates from the data in the message. In some examples, a customer may configure the system such that specific objects are created upon receiving a particular message. Additionally or alternatively, the customer may configure the system such that the system ignores creating the specific objects upon receiving the particular message.

For example, based on the storage data structure configured, the system may identify the message as being from a Health Information System (HIS) of a Hospital and being an A01 message type. Additionally, the system may map data contained in the message to object fields and change associated object states (e.g., new, active, inactive) as the message is processed. In some examples, at least some messages may have a prerequisite for an object to be in a specific state. For an incoming message identified as a patient object of an admit patient (e.g., A01) message type, the example systems and methods may have a prerequisite state as being 'New' and/or 'Active' because the patient has been previously registered in the system. As the admit patient message type is being processed, the patient object state is changed to 'Active' indicating that the patient is an active patient at a healthcare facility. Also, as the admit patient message type is being processed, the patient object may be updated with information contained in the admit patient type such as the patient ID, the entity, correlation, mapping, etc. For an incoming message identified as a register patient (e.g., A04) message type, the example systems and methods may expect that a patient object does not initially exist because the patient has not yet been registered in the system as being a patient. As the register patient message type is being processed, a patient object is created and the state is set as being "Active".

The examples described herein may restructure and/or aggregate associated lab and/or observation data received in different formats into one structured format (e.g., Extensible Markup Language) using one or more scripts deployed at run time. For example, first data received in a first format may be parsed and formatted in a structured format (e.g., tree structure having parent and child relationships) and second data received in a second format and associated with the first data may be parsed and formatted in the structured format and aggregated with the first data. Parsing the data enables relevant data to be identified and/or extracted and saved for future use. In some examples, an observation may include data in different objects including actual data, comments, reference ranges, etc. Using the examples described herein, data associated with the observation may be parsed and aggregated into one structured object useable in decision support and/or to collect patient data. In some examples, depending on the clinical data received, alerts may be generated to aid in decision support and added to a header at the parent level and/or the child level of the data structuring. In some examples, the data stored in the object may include codes and/or structures that are fully validated.

In some examples, a hook may be exposed in the process flow that dynamically introduces scripts that intercept the process flow and aggregate, modify, parse, filter, etc., data into a structured format based on the data received. The scripts may be customizable plugins executed at one or more stages within the process flow. One of the stages may be prior to the data being transformed into and/or mapped to the internal data structure (e.g., pre-mapping script) and/or one of the stages may be after the data has been transformed into and/or mapped to the internal data structure (post-mapping script). A script that may intercept the process flow after the data has been transformed into the internal data structure may be an appender plug-in script. In some examples, the appender plug-in script may append all observation values from incoming messages associated with the same observation (e.g., each having the same key code and/or Observation ID) into one string that may be stored as one object that is persisted by the system. Such an approach may be advantageous when observation values include carriage returns at their ends. Using the appender, the carriage returns may be filtered from the observation values. The observation values without the carriage returns may then be aggregated and/or appended for storage. In other examples, microbiology specimen observation data may be received in differently formatted segments. Using an example script, the segments may be aggregated, parsed to extract relevant information by separating out data embedded in text form, if applicable, and stored in a structured format. In some examples, data of related segments may be aggregated while unrelated segments may not.

The scripts may be displayed in a tree structure that may be selected by the user. The selected scripts may be executed based on the message type received without having to shut the system down. The scripts may be provided to the customer and/or the scripts may be written and/or modified by the customer, for example.

In some examples, data may be dynamically modeled based on the data and/or content received using an example customizable data structure modeling tool deployable without shutting the system down. The example tool may aggregate patient laboratory and/or observation data received from various systems and store this data in a customizable and/or dynamically configurable data structure. For example, the examples described herein may capture, parse and/or aggregate data (e.g., different segments) related to an observation and received from different sources into a unit of observation for storing in a structured fashion including codes and/or structures that may be fully validated. In some examples, alerts may be set up that aid in decision support based on the data received. The data, once stored, may be retrieved and/or used to aid in clinical decision support. Because data from different sources may be organized in a structured format, the examples described herein may aid in meaningful use stage 3 measures for a specific patient to arrive at national health statistics by the national health department.

In some examples, in-memory and/or persistent data storage may be created based on the dynamically configured data structure by searching a lookup for creating the specific data structure and persist. In some examples, in-memory and/or persistent data storage may be created based on data specified in an event to create objects and the content of the data received. Mapping between an event data schema and a data model may be customizable based on customer preferences and/or needs.

In some examples, based on an input message received, the example system identifies a service identifier code associated within the message and determines if there is a model specified for the identified code. If there is a specified model, the example system extracts the model from the message content and stores the model as a panel in memory. In some examples, based on an input message received, the example system identifies an observation identifier code and determines if there is a model specified for the identified code. If there is a specified model, the example system extracts the model from the message content and stores the model as an observation in memory.

FIG. 1 is a block diagram of an example healthcare environment 100 in which the example methods, apparatus, systems and/or articles of manufacture described herein to receive, process and/or structure healthcare information may be implemented. The example healthcare environment 100 includes a hospital 102 having a plurality of entities operating within and/or in association with the hospital 102. The hospital 102 includes a picturing archiving and communication system (PACS) 104, a laboratory information system 106, a cardiology department 108, a radiology information system (RIS) 110 and an oncology department 112. However, the hospital 102 may include more, less and/or different entities than depicted such as including a Healthcare Information System (HIS).

The cardiology department 108 includes cardiology-related healthcare practitioners, staff and devices and/or systems that support cardiology practices and treatments. The cardiology department 108 may have specific formats and/or structures in which healthcare documentation is generated, received, transmitted and/or processed. The oncology department 112 includes cancer-related healthcare practitioners, staff and devices and/or systems that support oncology practices and treatments. The oncology department 112 may have specific formats and/or structures in which healthcare documentation is generated, received, transmitted and/or processed that differ from the formats and/or structures used in connection with the cardiology department 108. In some examples, an Admit Discharge Transfer (ADT) message generated by the cardiology department 108 may be in a first format while a similar ADT message generated by the oncology department 112 may be in a second format. In some examples, an Observation Results Message (ORU) message generated by the cardiology department 108 may be a first format while a similar ORU message generated by the oncology department 112 may be in a second format. Such differences may also exist between any of the PACS 104, the laboratory information system 106, the RIS 110, etc.

The PACS 104 stores medical images (e.g., x-rays, scans, three-dimensional renderings, etc.) such as, for example, digital images in a database or registry. Images are stored in the PACS 104 by healthcare practitioners (e.g., imaging technicians, physicians, radiologists) after a medical imaging of a patient. Additionally or alternatively, images may be automatically transmitted from medical imaging devices to the PACS 104 for storage.

The RIS 110 stores data related to radiology practices such as, for example, radiology reports, messages, warnings, alerts, patient scheduling information, patient demographic data, patient tracking information, and/or physician and patient status monitors. Additionally the RIC 110 enables exam order entry (e.g., ordering an x-ray of a patient) and image and film tracking (e.g., tracking identities of one or more people that have checked out a film).

The laboratory information system 106 stores clinical information such as lab results, test scheduling information, corresponding practitioner(s), and/or other information related to the operation(s) of one or more labs at the corresponding healthcare facility. While example types of information are described above as being stored in certain elements of the hospital 102, different types of healthcare data may be stored in one or more of the entities 104-112. Further, the information stored in entities 104-112 may overlap and/or be combined into one or more of the entities 104-112. In some examples, the entities 104-112 of FIG. 1 may interact with an electronic medical record (EMR) system 114. The EMR 114 stores electronic copies of healthcare records associated with, for example, the hospital 102 and the entities 104-112 thereof.

The example healthcare environment 100 also includes an outpatient clinic 116. While two healthcare enterprises (e.g., the hospital 102, the outpatient clinic 116) are depicted in the healthcare environment of FIG. 1, the healthcare environment 100 may include any number (1, 2, 3, etc.) of similar or different healthcare enterprises. The example outpatient clinic 116 includes a lab information system 118 and a PACS 120 that operate similarly to the corresponding entities of the example hospital 102. The lab information system 118 and the PACS 120 of the example outpatient clinic 116 may generate, receive, transmit and/or process healthcare documentation differently than the hospital 102. Thus, differences in the formatting and/or structuring of healthcare information may exist between entities of a healthcare enterprise and/or between healthcare enterprises in general.

The hospital 102 and the outpatient clinic 116 are in communication with an Enterprise Clinical Information System (ECIS) (e.g., Qualibria) 122 via a network 124. The network 124 may be implemented by, for example, a wireless or wired Wide Area Network (WAN) such as a private network or the Internet, an intranet, a virtual private network, a wired or wireless Local Area Network, etc. More generally, any of the coupling(s) described herein may be via a network. Additionally or alternatively, the hospital 102 and/or the outpatient clinic 116 may be in communication with the ECIS 122 via direct or dedicated transmission mediums 126 and 128.

The ECIS 122 may support healthcare information processing implemented by systems, devices, application, etc., of the healthcare enterprises (e.g., the hospital 102, the outpatient clinic 116, etc.). The ECIS 122 is capable of processing messages, content, segments, etc., generated in connection with different healthcare enterprise entities (e.g., the entities 104-114, 118, 120) even if the messages, content, segments, etc., include different formats, structures, terminology, protocols, policies, etc.

In some examples, the processing of the ECIS 122 enables the interoperability of healthcare enterprise entities by aggregating data into standardized and/or structured formats and/or models that can then be used by all of the healthcare enterprise entities to assist in clinical decision support. In some examples, the ECIS 122 and, more specifically, an example message processing system 130 of the ECIS 122, may receive data including different message types (e.g., ADT:01, ADT:02, etc.) through a universal schema by accommodating all message variants (e.g., different HL7 messages). Additionally or alternatively, the message processing system 130 may intercept the process flow of incoming data using one or more scripts deployed at run time. The scripts may restructure, parse, modify and/or aggregate differently formatted data into one structured format (e.g., tree structure) more useable by the ECIS 122 and/or the healthcare enterprise entities. Additionally or alternatively, the message processing system 130 may map portions of incoming messages to different fields of different objects using the same of similar business logic regardless of the format of the messages received. Additionally or alternatively, the message processing system 130 may dynamically model data received into a customizable and/or dynamically configurable data structure. The data structured using the message processing system 130 may be stored in a data base or store 132. In some examples, the data base 132 may be a clinical data depository.

Figure 2:
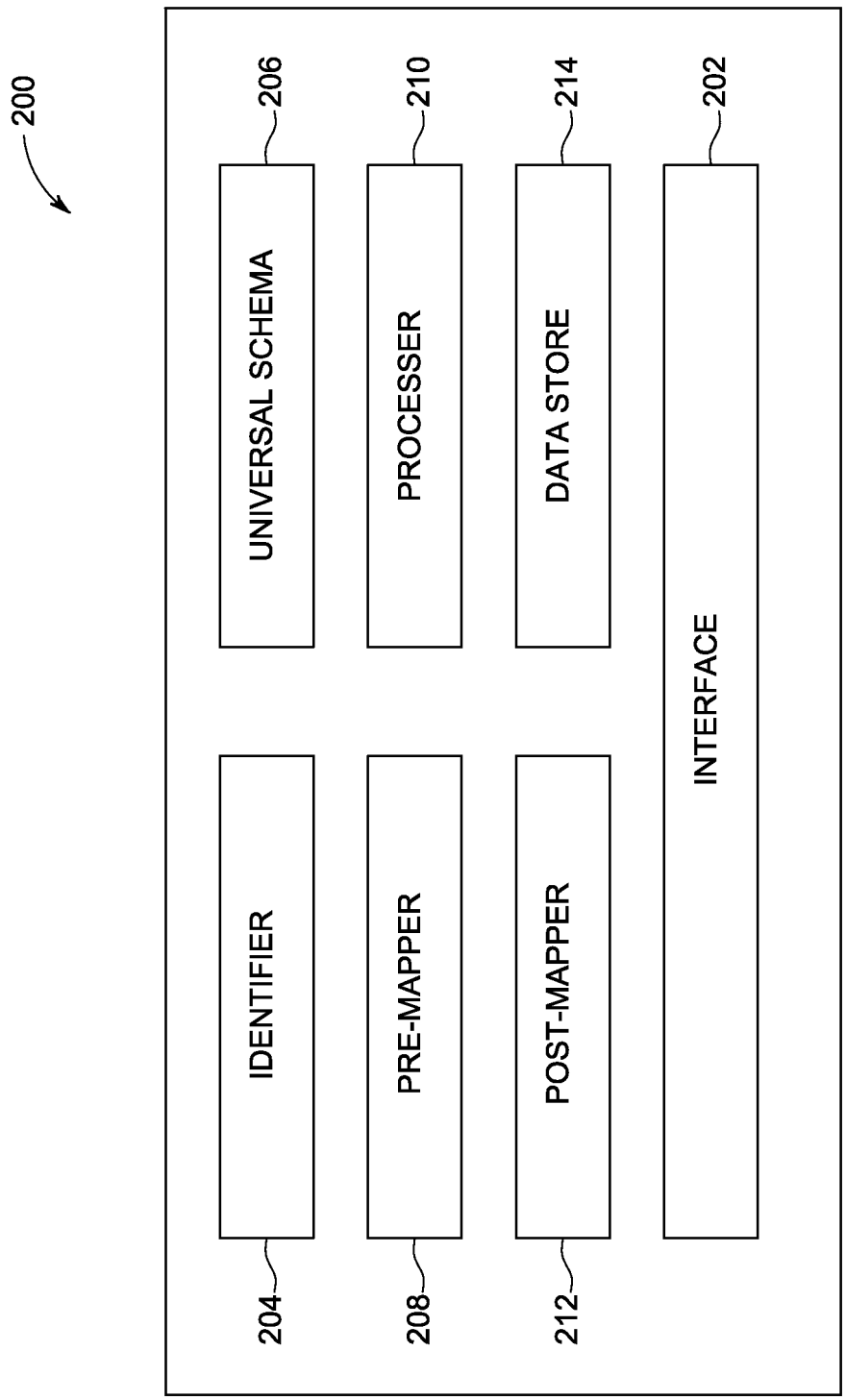
FIG. 2 is a block diagram of an example message processing system that may be used to implement the examples described herein.

FIG. 2 is a block diagram of an example message processing system 200 that may be used to implement the example message processing system 130 and/or the data base 132 of FIG. 1. In this example, the message processing system 130 includes an interface 202, an identifier 204, a universal schema 206, a pre-mapper 208, a processer 210, a post-mapper 212 and a data store 214. While an example manner of implementing the message processing system 130 and the data base 132 of FIG. 1 has been illustrated in FIG. 1, one or more of the elements, processes and/or devices illustrated in FIG. 2 may be combined, divided, re-arranged, omitted, eliminated and/or implemented in any other way. Further, the interface 202, the identifier 204, the universal schema 206, the pre-mapper 208, the processer 210, the post-mapper 212 and the data store 214, and/or, more generally, the example message processing system 200 of FIG. 2 may be implemented by hardware, software, firmware and/or any combination of hardware, software and/or firmware. Thus, for example, any of the interface 202, the identifier 204, the universal schema 206, the pre-mapper 208, the processer 210, the post-mapper 212 and the data store 214, and/or, more generally, the example message processing system 200 of FIG. 2 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the interface 202, the identifier 204, the universal schema 206, the pre-mapper 208, the processer 210, the post-mapper 212 and the data store 214, and/or, more generally, the example message processing system 200 of FIG. 2 are hereby expressly defined to include a tangible medium such as a memory, DVD, CD, etc., storing the software and/or firmware. Further still, the example message processing system 200 of FIG. 2 may include one or more elements, processes and/or devices in addition to, or instead of, those illustrated in FIG. 2, and/or may include more than one of any or all of the illustrated elements, processes and devices.

Generally, the example message processing system 200 enables data from disparate clinical systems of a healthcare organization to be centralized and/or formatted at one location in a standard format useable by clinicians, other applications, programs, etc. In some examples, the message processing system 200 may parse, filter, transform, aggregate, append, configure and/or modify the format and/or content of messages received from these disparate clinical systems into standardized and/or structured formats and/or models. This structured data may be displayed and/or used by clinicians using the interface 202, for example.

In some examples, as the message processing system 200 receives messages through, for example, the universal schema 206, the identifier 204 may identify the message type, formatting of and/or content contained within the message. The identifier 204 may identify the message as a ADT message type being in a first formatting, a second formatting, etc. The identifier 204 may identify content contained in the ADT message as including a first type of content, a second type of content, etc. The identifier 204 may identify the message as an ORU message type being in a first formatting, a second formatting, etc. The identifier 204 may identify content contained in the ORU message as identifying a first type of content, a second type of content, etc.

In some examples, prior to the message being processed, mapped and/or dynamically modeled using the processor 210, the pre-mapper 208 may apply one or more scripts to the incoming process flow. The scripts may filter, parse, modify, aggregate, etc., data received in different formats into one structured format that is more useable by the processor 210. For example, the message processing system 200 may receive messages made up of multiple segments in different formats and relating to the same observation. Using the pre-mapper 208, the multiple segments may be aggregated into a single object that is persisted within the message processing system 200. The single object may be formatted in a tree structure having parent and child relationships where the parent may include more general content and/or data and the child may include more detailed content and/or data. For example, multiple segments may be received relating to microbiology exam results. The microbiology exam results may include microbiology specimen and slide exams having qualitative data, quantitative data and/or comments embedded therein. Using the pre-mapper 208, the data of the microbiology exam results may be formatted in a tree structure such that specimen data is stored at a node associated with the specimen data, the microslide exam data is stored at a node associated with the microslide exam data and the qualitative data, the quantitative data and/or the comments are stored at respective nodes therein. The structured data may be saved at the data store 214 for later use, for example.

After the message is formatted at the pre-mapper 208 and/or if this formatting is not applicable and/or needed, the message may be processed using the processor 210. The processor 210 may dynamically model and/or configure data without having to shut the system down. The processor 210 may map, parse, filter, modify and/or aggregate, etc., patient data (e.g., ADT data, laboratory data, observation data, etc.) and/or content received from various systems and store this data in a customizable and/or dynamically configurable data structure at the data store 214. The data structure may be customized by a customer and/or provider using the interface 202, for example.

In some examples, the processor 210 may normalize the data and/or content of the message by mapping. The mapping may be customizable based on customer preferences and/or needs using the interface 202, for example. This normalized data may then be translated and stored in a structured format, model, panel, etc., usable in clinical decision support. For example, based on the identifier 204 identifying messages as being from a Healthcare Information System (HIS) of a Hospital and being an A01 message type, the processor 210 may map and/or extract data from the messages to fields of one or more objects associated with A01 message types where the data may then be saved in a structured format at the data store 214 for later use.

For example, based on the identifier 204 identifying messages as being from a Cardiology Department of a Hospital and being observation messages, the processor 210 may map and/or extract data from the messages to one or more observation items in a panel and/or sub-panel associated with the observation messages where the data may then be saved in a structured format at the data store 214 for later use. However, if there is no panel associated with the observation messages, the data may be stored as observation items in a structured format at the data store 214 for later use, for example.

For example, based on the identifier 204 identifying messages as being from an Oncology Department and being laboratory messages, the processor 210 may map and/or extract data from the messages to generate a model associated with laboratory messages where the data may then be saved in a structured format at the data store 214 for later use. In some examples, the mapped data from different sources and/or in different formats may be parsed and/or aggregated into a single unit for storing in a structured fashion including codes and/or structures that may be fully validated.

After the message has been processed using the processor 210, the post-mapper 212 may apply one or more scripts to the process flow. The scripts may filter, parse, modify, aggregate data received. For example, observation values including carriage returns at their ends may be filtered using the post-mapper 212 to remove the carriage returns. The filtered observation values may then be appended for storage at the data store 214, for example.

The message processing system 200 may include one or more internal memories and/or data stores including the data store 214. Data storage can include any variety of internal and/or external memory, disk, remote storage communicating with the message processing system 200. In some examples, the interface 202 may be configured as a graphical user interface (GUI).

Figure 3:
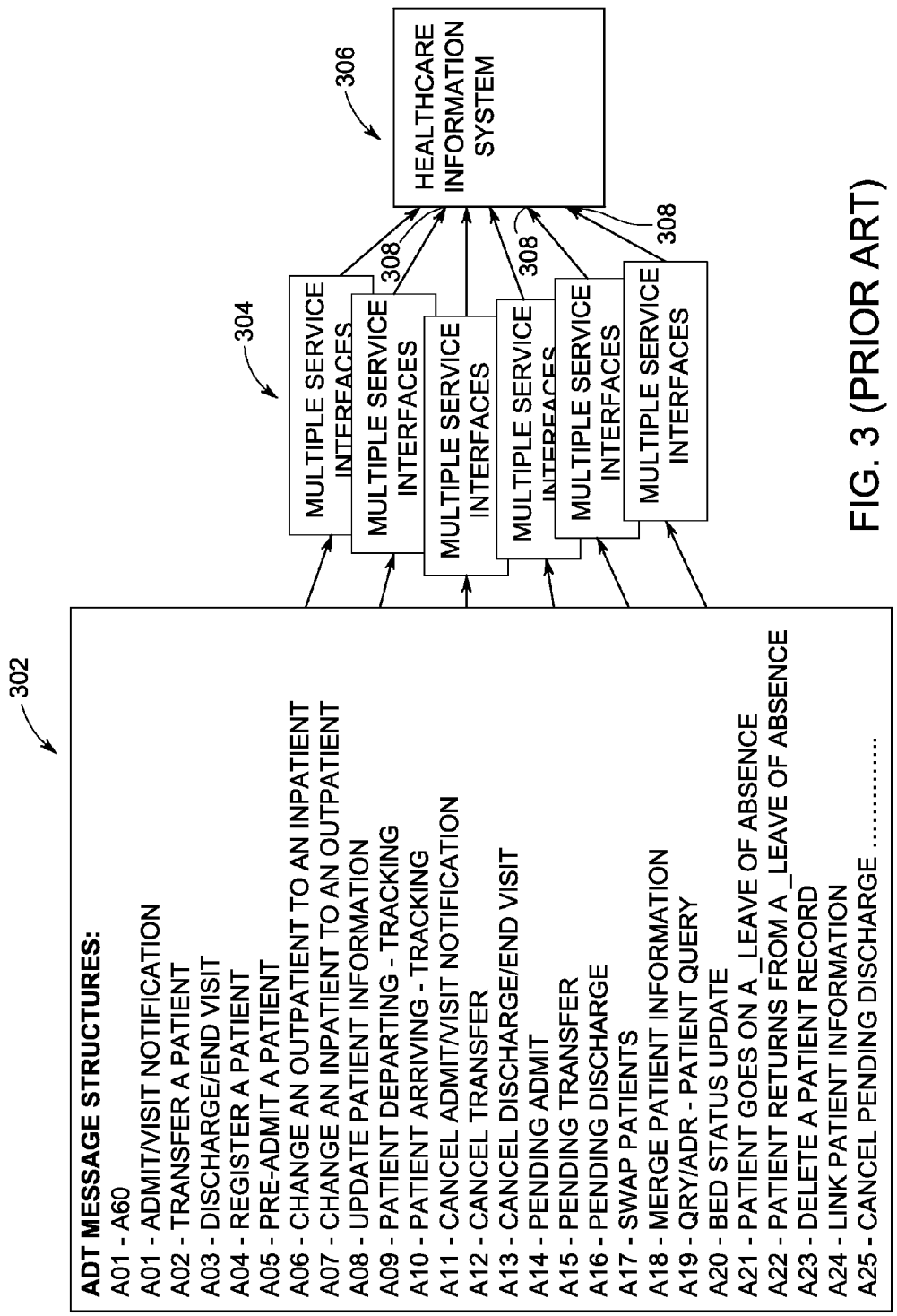
FIG. 3 depicts messages being routed through a plurality of known service interfaces.

FIG. 3 depicts a plurality of ADT message structures 302 being routed through a plurality of known service interfaces, sub-schemas and/or schemas 304 to a healthcare information system 306. Multiple service interfaces 304 are being used because the incoming ADT messages (e.g., A01, A02, etc.) may be differently formatted and/or have less, more and/or different fields associated therewith. Including numerous service interfaces 304 creates numerous interface end points 308 whose maintenance is time and labor intensive.

Figure 4:
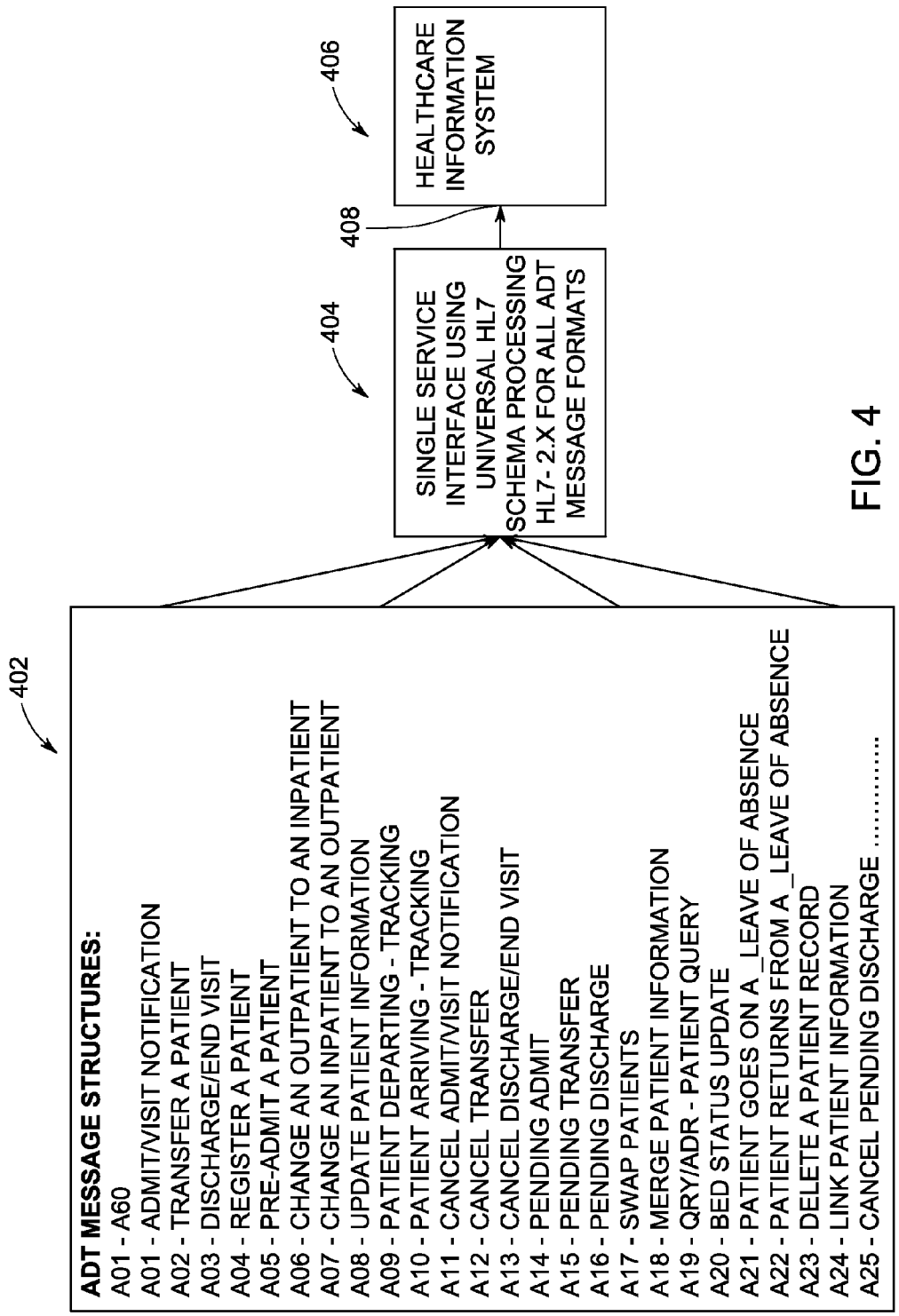
FIG. 4 depicts messages being routed through an example universal schema.

FIG. 4 depicts a plurality of ADT message structures 402 being routed through an example "universal" or uniform schema (e.g., universal XML schema) 404 to a healthcare information system 406. In some examples, the universal schema 404 may be used to process all versions and/or triggers of HL7 messages (e.g., ADT message, ORU messages, MDM messages, etc.). In some examples, the universal schema 404 includes an expansive messaging framework that accommodates any variant of an HL7 message structure and/or fields associated with the various versions of HL7. For example, the universal schema 404 may aggregate all fields of each of the HL7 ADT message structures and/or the fields associated with the various versions of 2.x HL7 ADT messages by not restricting and/or requiring fields that may not be supported across all HL7 versions and/or HL7 structures. By using the universal schema 404 instead of the multiple service interfaces 304 of FIG. 3, the number of interface end points 408 at the healthcare information system 406 is significantly reduced, which in turn reduces the time and labor intensity of maintaining such systems.

Figure 5:
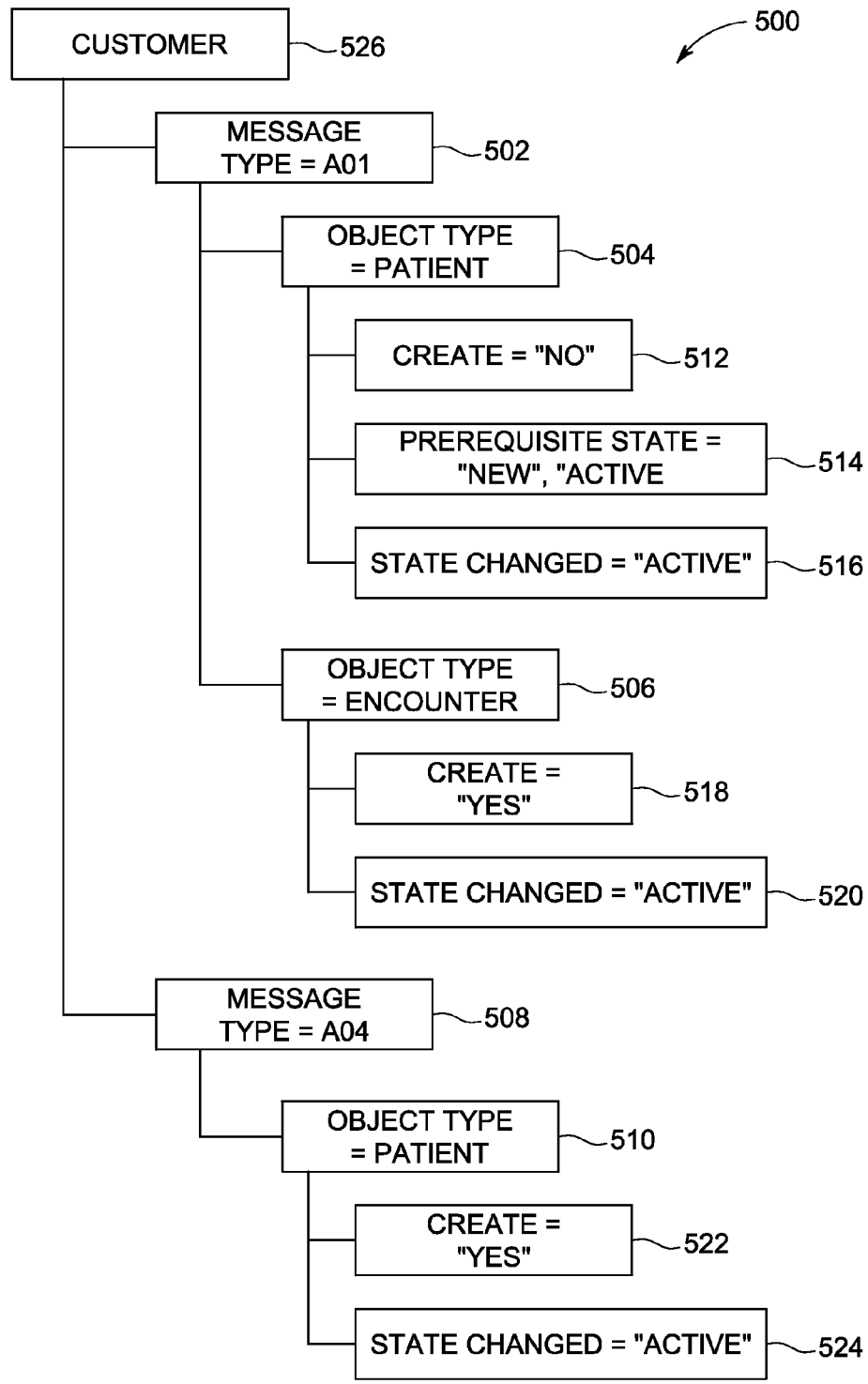
FIG. 5 depicts an example tree structure that may be used in connection with the examples described herein.

FIG. 5 depicts an example tree structure 500 having parent and child relationships in which messages may be mapped, routed, configured, formatted, structured and/or stored. In this example, the tree structure 500 includes parent nodes 502-510 and child nodes 512-524. However, in other examples, the tree structure 500 may include less, more and/or different nodes. The node 502 is related to A01 message types, the node 504 is related to a patient object type of the A01 messages and the nodes 512-516 relate to fields of the patient object type whose state may change as a message is manipulated through the object states. The node 506 is related to an encounter object type and nodes 518 and 520 relate to fields of the encounter object type whose state may change as a message is manipulated through the object states. The node 508 is related to A04 message types, the node 510 is related to a patient object type of the A04 messages and the nodes 522 and 524 relate to fields of the patient object type whose state may change as a message is manipulated through the object states.

In some examples, a message received from a customer (e.g., Mayo Clinic®) 526 may be identified as an A01 message type and may be mapped to the node(s) 502, 504 and/or 506, accordingly. In some examples, for A01 messages types, the patient object type may have a prerequisite state as being 'New' and/or 'Active' at node 514 because the system expects that the patient has been previously registered in the system. As the A01 message type is being processed, the patient object state may be changed to 'Active' at node 516 indicating that the patient is an active patient at a healthcare facility. Additionally, as the A01 message is being processed, data and/or content associated therewith may be aggregated, formatted, etc. into the structured format of the tree structure 500, for example.

In some examples, a message received from the customer (e.g., Intermountain Healthcare) 526 may be identified as an A04 message type and mapped to the node(s) 508 and/or 510, accordingly. In some examples, for A04 messages, the patient object type may not expect the patient object to initially exist because the patient has not been registered in the system as being a patient at a healthcare facility. As the register patient type message is processed, the patient object is created at node 522 and the state is then changed to 'Active' at node 524.

In some examples, a data structure of an example system associated with the tree structure 500 may be manipulated and/or customized by a customer and/or provider using a configuration user interface. In some examples, an example system associated with the tree structure 500 may dynamically define a storage data structure (e.g., the tree structure 500). In some examples, an example system associated with the tree structure 500 may receive any type of input data by defining a schema and/or formatting at run time.

In some examples, the tree structure 500 may be associated with business logic that maps, formats and/or structures messages received in different formats from different customers, applications and/or programs. The business logic may be dynamically defined at run time. This business logic of the examples described herein may be the same and/or similar for all customers even if those customers use different message formats, applications and/or systems. Thus, new and/or existing clients or customers may be synchronized such that their incoming messages are mapped, formatted, configured, etc., without the underlying business logic of the system being changed, for example.

Figure 6:
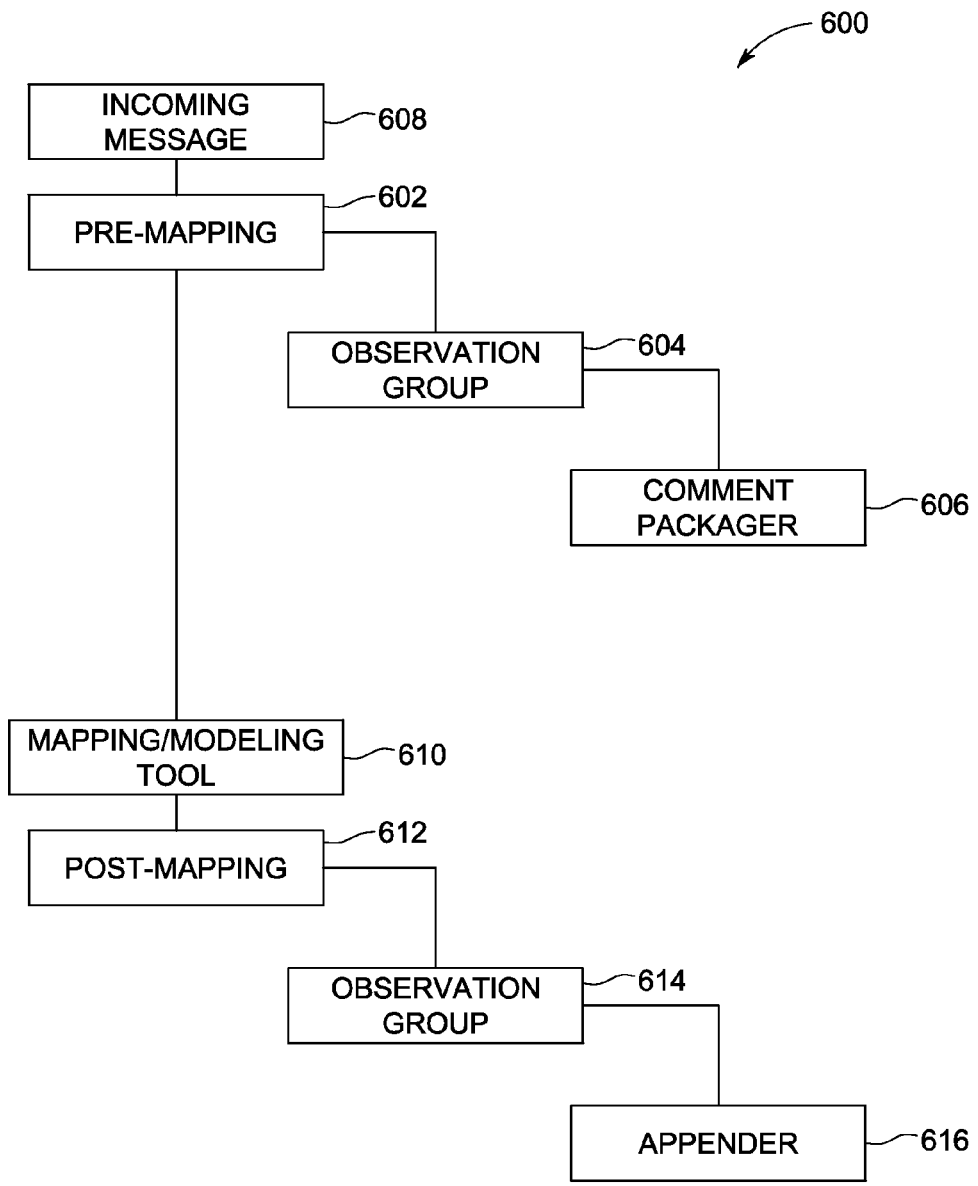
FIG. 6 depicts example architecture that may be used to implement the examples described herein.

FIG. 6 depicts an example architecture 600 including scripts based on a customer. In some examples, the architecture 600 may include a pre-mapping plug-in 602 that may introduce scripts to incoming messages. The scripts may filter, append, parse and/or aggregate data and/or content of incoming messages to format and/or structure the data and/or content into a more useable form. In some examples, a plurality of plug-in scripts (e.g., an observation group 604, a comment packager 606) may be available in a library for use by a customer (e.g., administrator) and/or provider. In other examples, plug-in scripts may be written and/or modified by the customer and/or provider and added to the library.

In this example, the pre-mapping plug-in 602 includes the observation order or group 604 and the comment packager 606. The observation order or group 604 may represent incoming data structures for an observation(s) on which one or more of the scripts are to act on, for example. The comment packager 606 may identify, aggregate and/or combine comments from various data structures of an associated observation (e.g., the same observation) and append the combined data into a field of the storage data structure, for example.

In some examples, an incoming message 608 may include a first segment relating to a microbiology observation in a first data structure and a second segment including additional specimen data in a second structure. Using the pre-mapping plug-in 602, the incoming message 608 may be aggregated and parsed, if applicable, into a standard data structure. In some examples, parsing may include separating out data embedded in a text form in the segments. In some examples, the data may be aggregated and formatted into the standard data structure by adding one or more scripts specific to the incoming message type, format and/or customer from which the message is received.

The architecture 600 may include an example mapping/modeling tool 610 that maps and/or aggregates data received from various systems and stores the data in a customizable and/or dynamically configurable data structure in a repository holding medical information. Using, for example, OSGI (e.g., open services gateway initiative), the mapping/modeling tool 610 may apply changes made to the mapping and/or structuring of data at runtime without applying any patches (e.g., custom patches generated by the manufacturer at the customer's request) to the code. In some examples, the data may be processed using the mapping/modeling tool 610 after applying the script(s) of the pre-mapping plug-in 602.

In some examples, the mapping/modeling tool 610 enables customized mapping between event data schema and a data model. In some examples, the mapping/modeling tool 610 may capture and/or aggregate data contained in segments related to an observation and received from different sources into a unit of observation that may be parsed for storing in a structured format. The data in the structured and/or consistent format may include codes and/or structures that are fully validated. The data, once stored, may be advantageously used in decision support. In some examples, alerts may be set up that alert customers and/or providers when data received varies from a standard.

The architecture 600 may include post-mapping plug-ins 612 that may introduce scripts to the data after being processed using the mapping/modeling tool 610. The scripts may filter, append, parse and/or aggregate data and/or content prior to its storage, for example. In some examples, a plurality of plug-in scripts (e.g., an observation group 614, an appender 616) may be available in a library for use by a customer and/or provider. In some examples, plug-in scripts may be written and/or modified by the customer and/or provider and added to the library.

In some examples, the post-mapping plug-ins 612 includes the observation order or group 614 and the appender 616. The observation order or group 604 may represent data structures for an observation(s) on which one or more of the scripts are to act on, for example. The appender 616 may append observation values for incoming observation messages associated with the same observation into an object that gets persisted within the system. For example, observation values including carriage returns at their ends may be filtered using the appender 616 to remove the carriage returns. The filtered observation values may then be appended for storage, for example.

Figure 7:
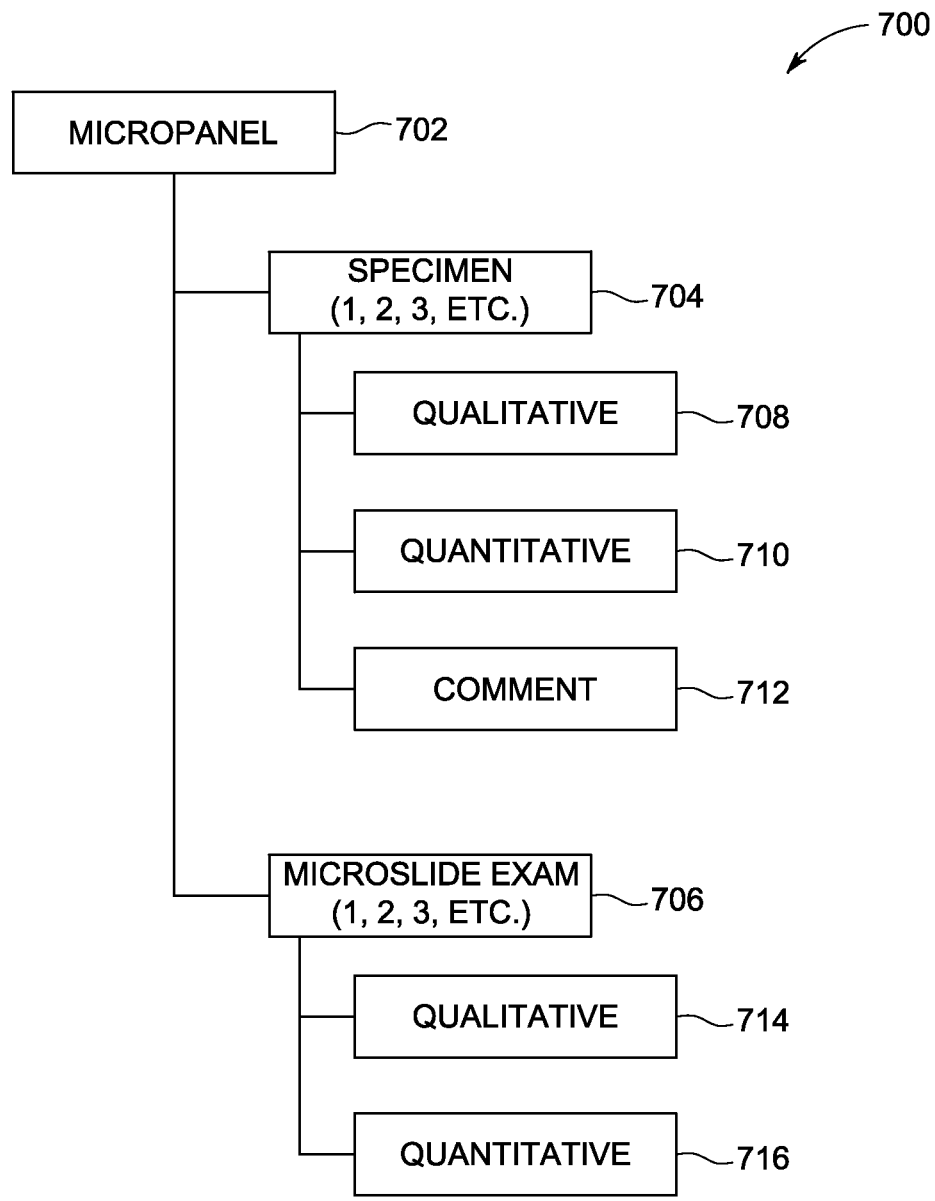
FIG. 7 depicts an example tree structure that may be used in connection with the examples described herein.

FIG. 7 depicts an example tree structure 700 having parent and child relationships in which messages may be aggregated, filtered, parsed, formatted, structured and/or stored using an example pre-mapping plug. In this example, the tree structure 700 includes parent nodes 702, 704 and 706 and child nodes 708-716. However, in other examples, the tree structure 700 may include less, more and/or different nodes. The node 702 is related to a micropanel and the node 704 is related to specimen data including qualitative data at node 708, quantitative data at node 710 and comments at node 712. The node 706 relates to microslide exam data including qualitative data at node 714 and quantitative data at node 716.

In some examples, an incoming message may include multiple segments all related to a microbiology specimen. Some of the segments may include qualitative data, some of the segments may include quantitative data and some of the segments may include comments. By applying pre-mapping scripts, qualitative data may be filtered, aggregated, combined and/or parsed and stored at node 708, quantitative data may be filtered, aggregated, combined and/or parsed and stored at node 710 and comment data may be filtered, aggregated, combined and/or parsed and stored at node 712.

In some examples, an incoming message may include multiple segments relating to a microslide exam. Some of the segments may include quantitative data and some of the segments may include qualitative data. By applying pre-mapping scripts, qualitative data may be filtered, aggregated, combined and/or parsed and stored at node 714 and quantitative data may be filtered, aggregated, combined and/or parsed and stored at node 716. In other examples, multiple segments may be received including microbiology specimen data and microslide exam data.

FIGS. 8-16 depict example flow diagrams representative of processes that may be implemented using, for example, computer readable instructions that may be used to map and/or model data within a healthcare system. The example processes of FIGS. 8-16 may be performed using a processor, a controller and/or any other suitable processing device. For example, the example processes of FIGS. 8-16 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 8-16 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 8-16 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 8-16 may be implemented manually or as any combination(s) of any of the foregoing techniques, for example, any combination of firmware, software, discrete logic and/or hardware. Further, although the example processes of FIGS. 8-16 are described with reference to the flow diagrams of FIGS. 8-16, other methods of implementing the processes of FIGS. 8-16 may be employed. For example, the order of execution of the blocks may be changed, and/or some of the blocks described may be changed, eliminated, sub-divided, or combined. Additionally, any or all of the example processes of FIGS. 8-16 may be performed sequentially and/or in parallel by, for example, separate processing threads, processors, devices, discrete logic, circuits, etc.

Figure 8:
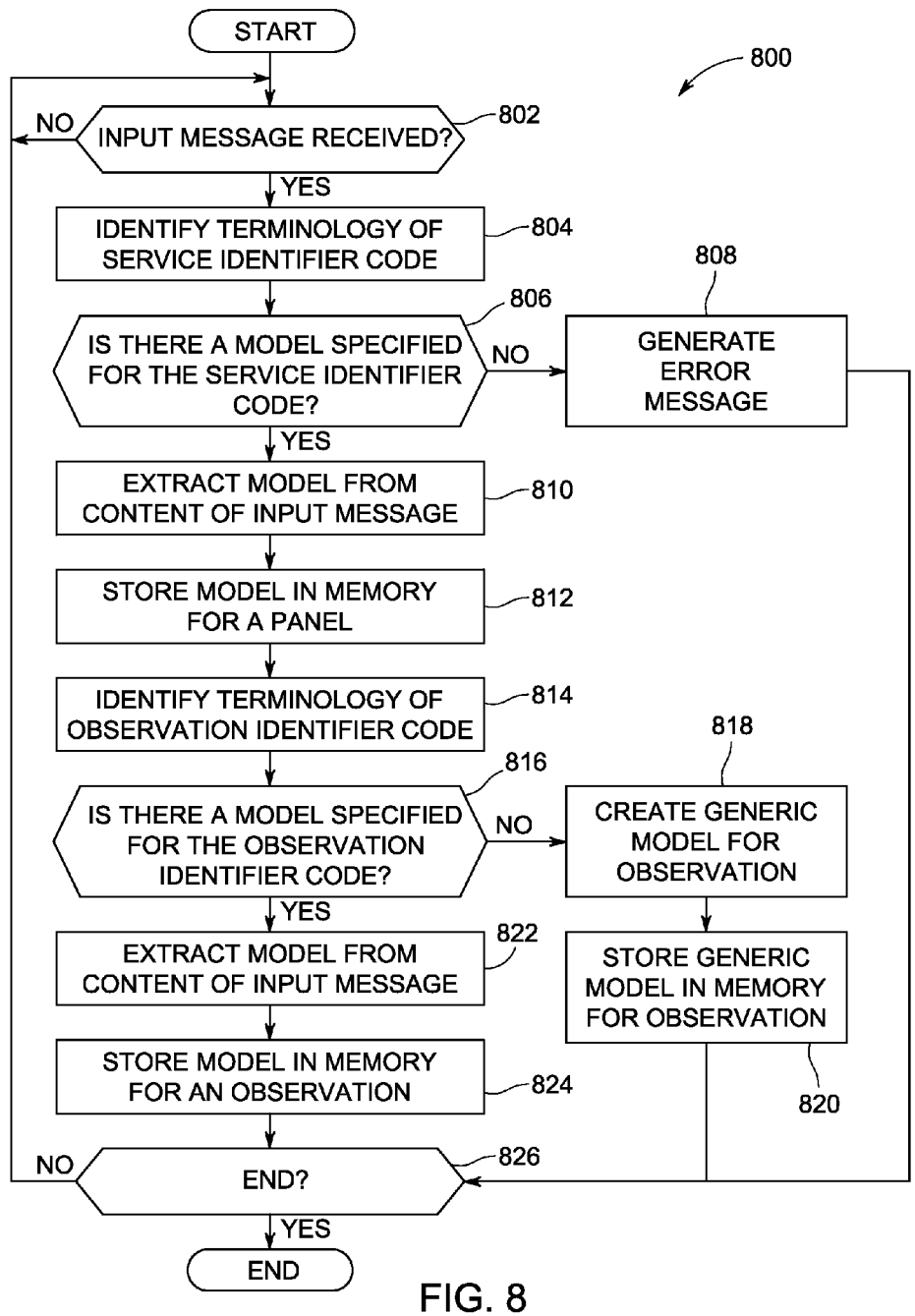
FIGS. 8-16 are flow diagrams of example methods that can be used to implement the examples described herein.

FIG. 8 depicts an example flow diagram 800 that enables data of incoming messages to be mapped, dynamically modeled and/or stored in a structured format. At block 802, the method 800 determines if an input message has been received. The incoming message may be an ORU message including observation data, laboratory data, etc. If an incoming message has been received, at block 804, the method 800 identifies terminology of a service identifier code (e.g., OBR-4.1) associated with the message. At block 806, the method 800 determines if there is a model specified for and/or associated with the identified service identifier code (e.g., is there a model specified for the OBR-4.1). If there is no model associated with the identified service identifier code, control moves to block 808 where an error message may be generated.

However, if the method 800 identifies a model associated with the identified service identifier code, control moves to block 810 and the method 800 extracts the associated model from content of the message. At block 812, the method 800 may store the extracted model in memory for a panel.

At block 814, the method 800 may identify terminology of an observation identifier code (e.g., OBX 3.2) associated with the message. At block 816, the method 800 determines if there is a model specified for the identified observation identifier code (e.g., is there a model specified for the OBX 3.2). If the method 800 determines that there is no model specified for the identified observation identifier code, control moves to block 818 and the method 800 creates a generic model for an observation and at block 820 the model is stored in memory for the observation.

However, if the method 800 determines that a model is specified for the identified observation identifier code, control moves to block 822 and the method 800 extracts the associated model from content of the message. At block 824, the method 800 may store the extracted model in memory for an observation. At block 826, the method 800 determines whether or not to return to block 802. Otherwise the example method 800 is ended.

Figure 9:
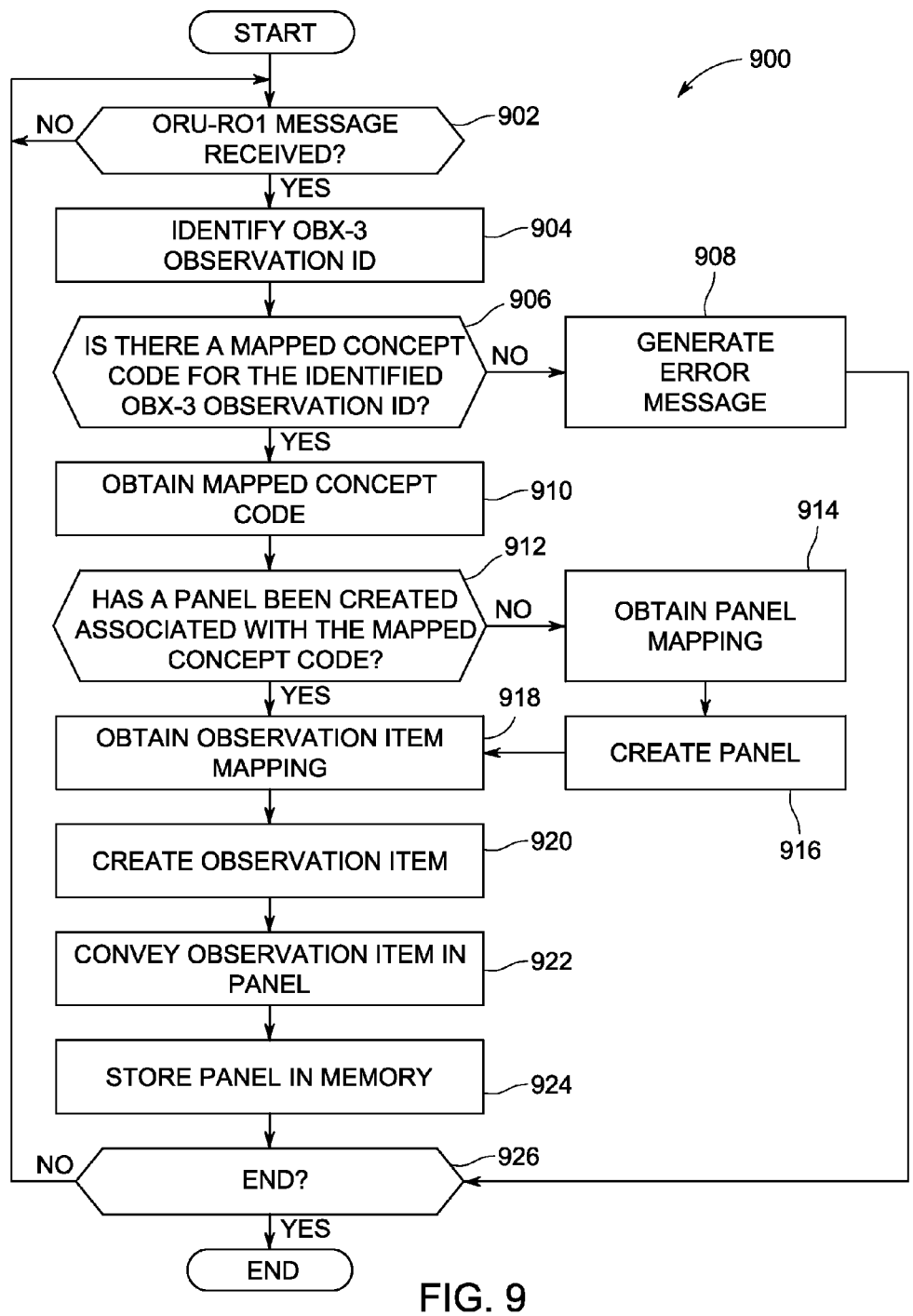

FIG. 9 depicts an example flow diagram 900 that enables data of incoming messages to be mapped, dynamically modeled and/or stored in a structured format. In some examples, the method 900 may be used to process observations with panel. At block 902, the method 900 determines whether or not an ORU-R01 message has been received. If such a message has been received, control moves to block 904 and the method 900 identifies an OBX-3 Observation ID associated with the message. At block 906, the method 900 determines if there is a mapped concept code for the identified OBX-3 Observation ID. If the method 900 does not identify a mapped concept code, control moves to block 908 and the method 900 generates an error message.

However, if the method 900 identifies a mapped concept code, control moves to block 910 and the method 900 obtains the mapped concept code for the identified OBX-3 Observation ID. At block 912, the method 900 determines if a panel has been created that is associated with and/or that the mapped concept code points to. In some examples, the panel may be a blood pressure panel including items such as systolic blood pressure measurements, diastolic blood pressure measurements, mean arterial pressure measurements, etc. In some examples, the panel may be a urine output panel including items such as output volume measurements, fluid description evaluation, etc. If the method 900 determines that no panel has been created, control moves to block 914 and the method 900 obtains panel mapping and at block 916 the method 900 creates a panel.

At block 918, the method 900 obtains observation item mapping and at block 920 the method 900 creates an observation item using, for example, data contained in the message. At block 922, the method 900 conveys and/or puts the observation item into the associated panel and at block 924 the method 900 stores the panel in memory. At block 926, the method 900 determines whether or not to return to block 902. Otherwise the example method 900 is ended.

Figure 10:
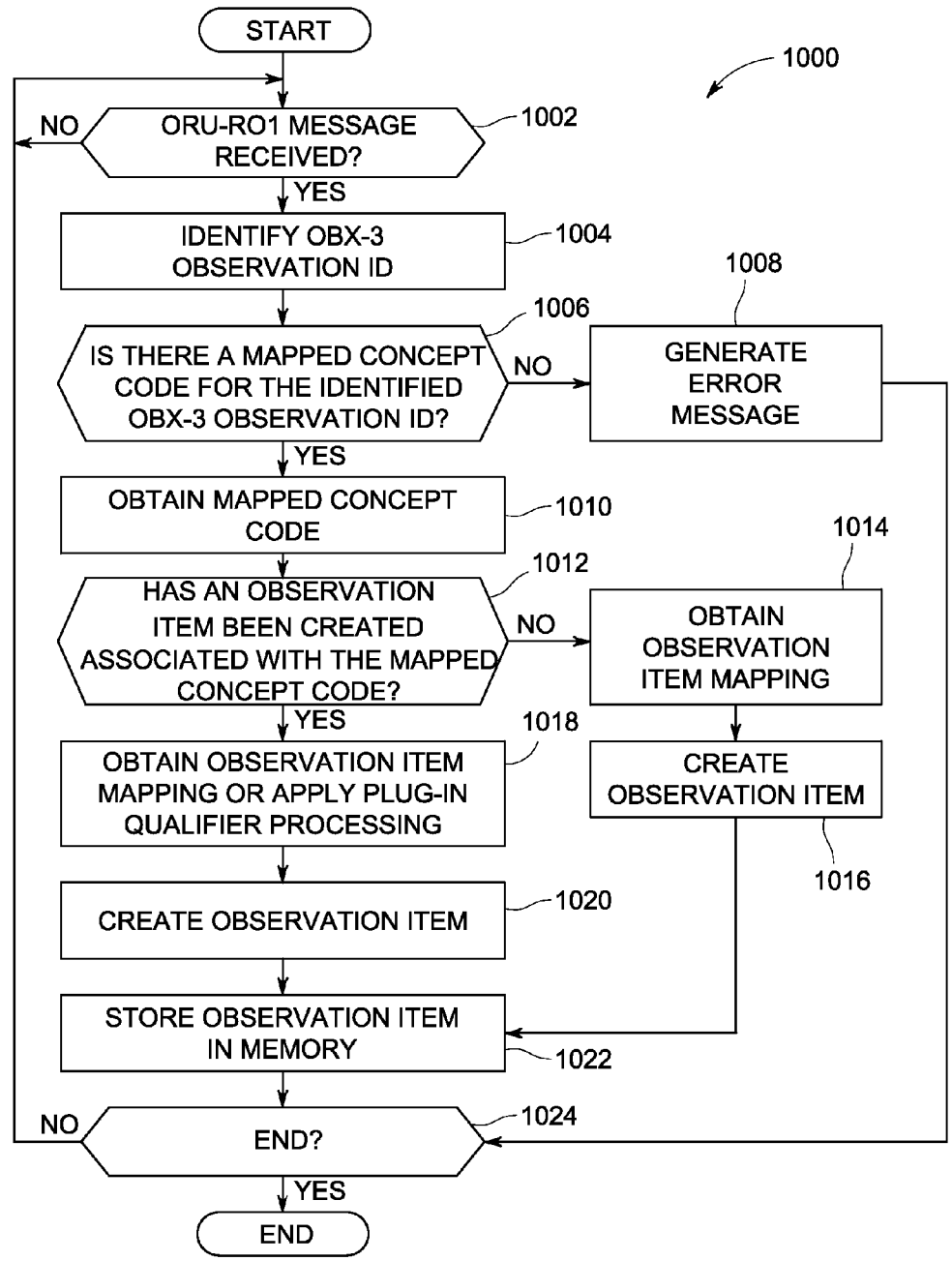

FIG. 10 depicts an example flow diagram 1000 that enables data of incoming messages to be mapped, dynamically modeled and/or stored in a structured format. In some example, the method 1000 may be used to process observations including multiple segments into one model with no panel. At block 1002, the method 1000 determines whether or not an ORU-R01 message has been received. If such a message has been received, control moves to block 1004 and the method 1000 identifies an OBX-3 Observation ID associated with the message. At block 1006, the method 1000 determines if there is a mapped concept code for the identified OBX-3 Observation ID. If the method 1000 does not identify a mapped concept code, control moves to block 1008 and the method 1000 generates an error message.

However, if the method 1000 identifies a mapped concept code, control moves to block 1010 and the method 1000 obtains the mapped concept code for the identified OBX-3 Observation ID. At block 1012, the method 1000 determines if an observation item has been created that is associated with and/or that the mapped concept code points to. In some examples, the observation item may be temperature measurements, ventilator vasoactive agents or blood pressure. If the method 1000 determines that no observation item has been created, control moves to block 1014 and the method 1000 obtains observation item mapping and at block 1016 the method 1000 creates an observation item using, for example, data contained in the message.

At block 1018, the method 1000 obtains observation item mapping and/or applies plug-in qualifier processing. At block 1020, the method 1000 creates an observation item using, for example, data contained in the message. At block 1022, the method 1000 stores the observation item in memory. At block 1024, the method 1000 determines whether or not to return to block 1002. Otherwise the example method 1000 is ended.

Figure 11:
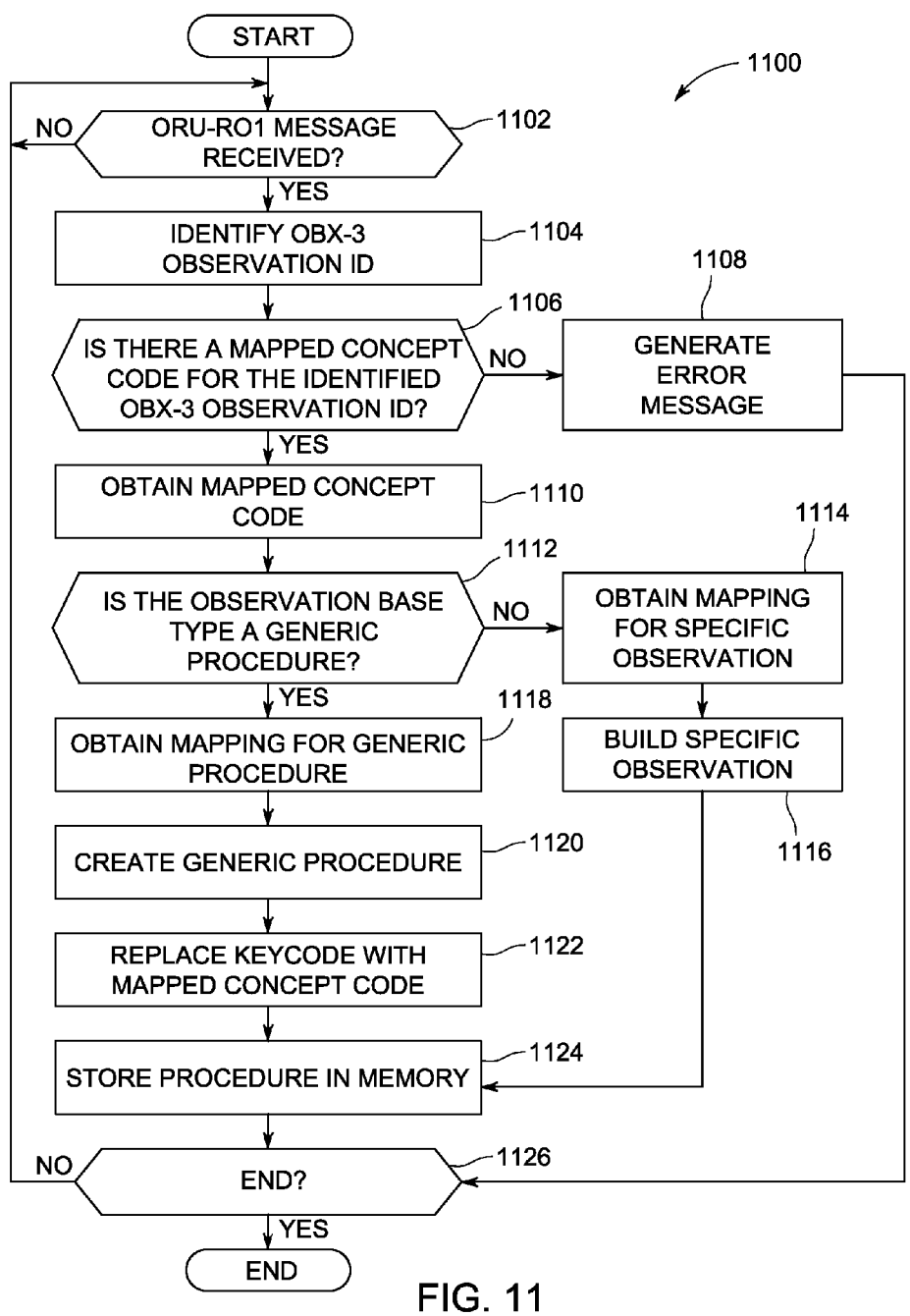

FIG. 11 depicts an example flow diagram 1100 that enables data of incoming messages to be mapped, dynamically modeled and/or stored in a structured format. In some example, the method 1100 may be used to process observations with no panel. At block 1102, the method 1100 determines whether or not an ORU-R01 message has been received. If such a message has been received, control moves to block 1104 and the method 1100 identifies an OBX-3 Observation ID associated with the message. At block 1106, the method 1100 determines if there is a mapped concept code for the identified OBX-3 Observation ID. If the method 1100 does not identify a mapped concept code, control moves to block 1108 and the method 1100 generates an error message.

However, if the method 1100 identifies a mapped concept code, control moves to block 1110 and the method 1100 obtains the mapped concept code and/or mapping for the identified OBX-3 Observation ID. At block 1112, the method 1100 determines if the observation base type is a generic procedure. In some examples, the generic procedure may be associated with ventilator mode evaluations, breath setting rate measurements, respiratory rate measurements, positive end expiatory pressure setting measurements, expired corrected machine tidal volume measurements, fraction of inspired oxygen measurements, pressure support setting measurements, heart rate measurements, central venous pressure measurements, etc. If the method 1100 determines that the observation base type is not a generic procedure, control moves to block 1114 and the method 1100 obtains mapping for the specific observation associated with the message. At block 1116 the method 1100 builds a specific observation.

However, if the method 1100 determines that the observation base type is a generic procedure, control moves to block 1118 and the method 1100 obtains mapping for the generic procedure. At block 1120, the method 1100 creates and/or builds a generic procedure associated with the message. In some examples, the procedure may be associated with a single valvular procedure (e.g., AVR, MVR, TVR, etc.), a coronary bypass surgery (e.g., CABG), septal myectory, proximal ascending aorta aneurysm repair without circular arrest, etc. At block 1122, the method 1100 replaces a key code (e.g., CEType key code) with the mapped concept code associated with the OBX-3 Observation ID. At block 1124, the method 1100 stores the procedure and/or associated information in memory. At block 1126, the method 1100 determines whether or not to return to block 1102. Otherwise the example method 1100 is ended.

Figure 12:
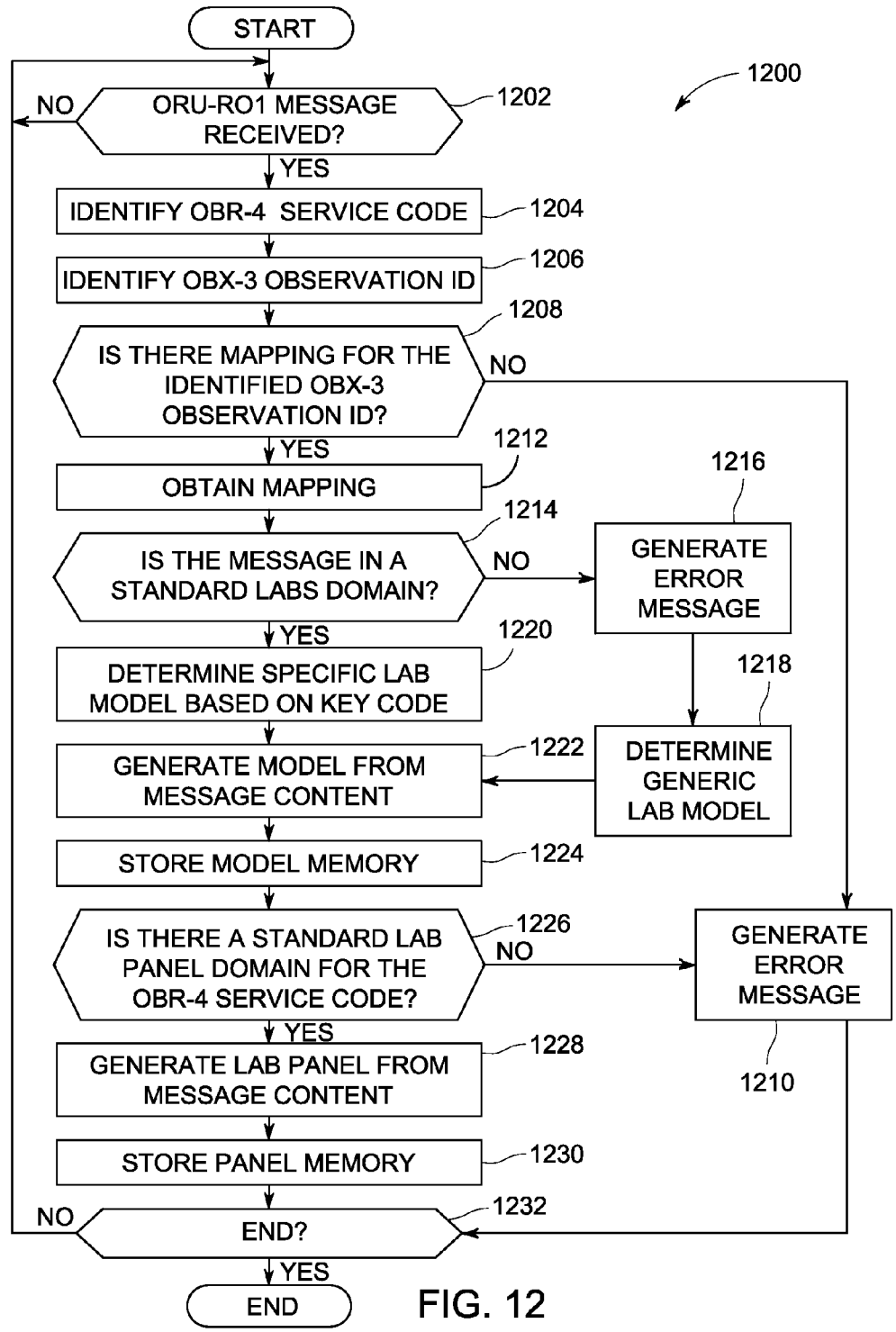

FIG. 12 depicts an example flow diagram 1200 that enables data of incoming messages to be mapped, dynamically modeled and/or stored in a structured format. In some example, the method 1200 may be used to process laboratory data. At block 1202, the method 1200 determines whether or not an ORU-R01 message has been received. If such a message has been received, control moves to block 1204 and the method 1200 identifies a OBR-4 service code (e.g., universal OBR-4 service code) associated with the message. At block 1206, the method 1200 identifies an OBX-3 Observation ID associated with the message. At block 1208, the method 1200 determines if there is mapping for the OBX-3 Observation ID and/or if there is mapping in the ECIS Terminology namespace. If the method 1200 does not identify mapping for the OBX-3 observation ID, control moves to block 1210 and the method 1200 generates an error message.

However, if the method 1200 identifies mapping for the OBX-3 observation ID, control moves to block 1212 where such mapping is obtained. At block 1214, the method 1200 determines if the message is in the standard lab domain and/or lab observations domain. If the message is not in the standard lab domain and/or lab observations domain, control moves to block 1216 and the method 1200 generates an error message. At block 1218, the method 1200 determines which generic lab model is associated with the message. In some examples, the method 1200 may identify an OBX-2 value type associated with the message and use the OBX-2 value type to determine the data type of a result such as the data being in a standard laboratory observations quantitative model, standard laboratory observations coded model, standard laboratory observations narrative model, etc.

However, if the method 1200 determines that the message is in the standard lab domain and/or laboratory observations domain, control moves to block 1220 and the method 1200 determines the specific lab model based on a key code, relationship context, etc. associated with the message, for example. At block 1222, the method 1200 generates a model from the message content and at block 1224 the method 1200 stores the model in memory.

At block 1226, the method 1200 determines if there is a standard lab panel domain for the OBR-4 service code (e.g., does the code exist in the standard lab panel domain). If there no standard lab panel for the OBR-4 service code, control moves to block 1210 and the method 1200 generates an error message. However, if there is a standard lab panel for the OBR-4 service code, control moves to block 1228 and the method 1200 generates a lab panel from the message content. At block 1230, the method 1200 stores the panel in memory and at block 1232 the method 1200 determines whether or not to return to block 1202. Otherwise the example method 1200 is ended.

Figure 13:
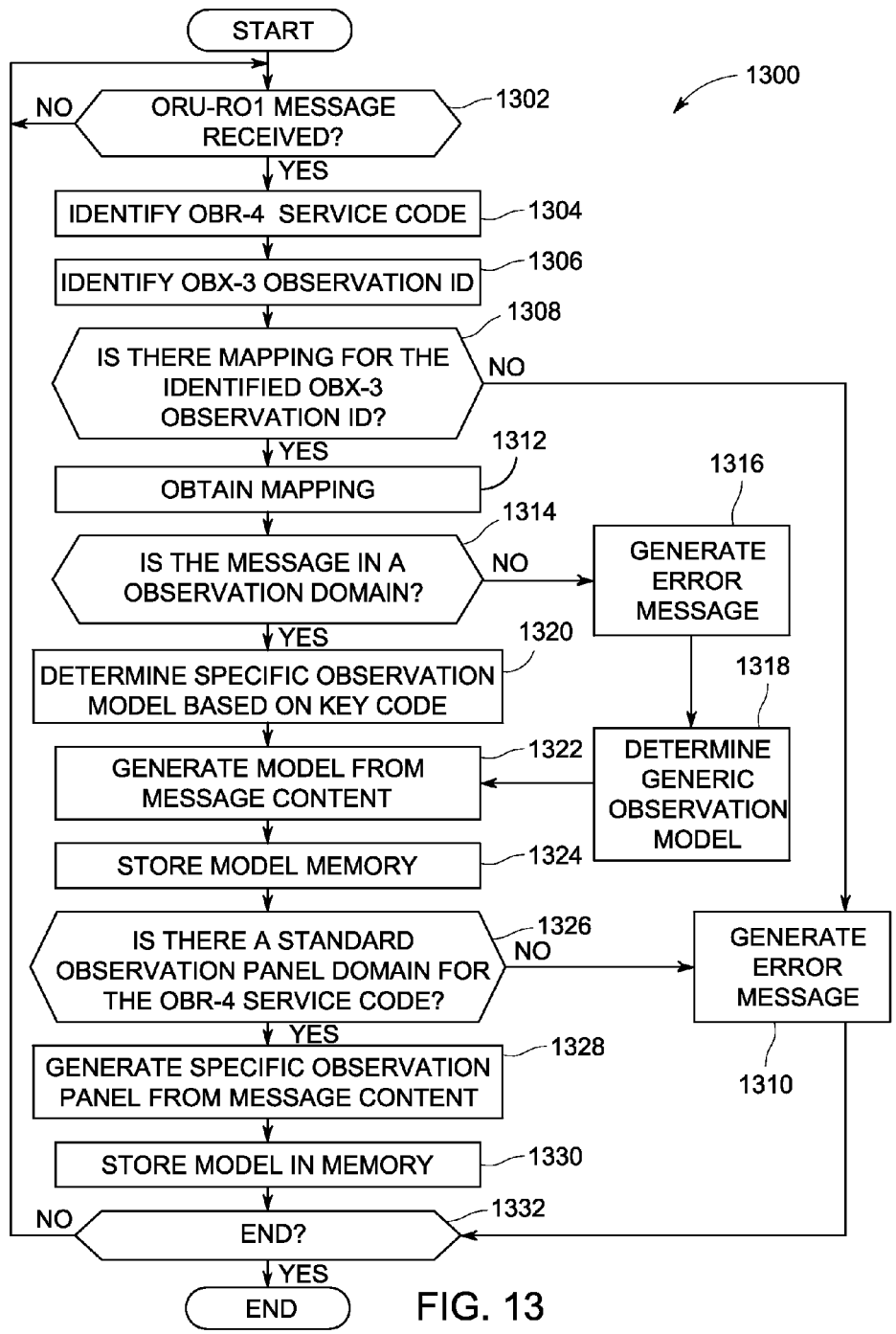

FIG. 13 depicts an example flow diagram 1300 that enables data of incoming messages to be mapped, dynamically modeled and/or stored in a structured format. In some example, the method 1300 may be used to process observation data. At block 1302, the method 1300 determines whether or not an ORU-R01 message has been received. If such a message has been received, control moves to block 1304 and the method 1300 identifies a OBR-4 service code (e.g., universal OBR-4 service code) associated with the message. At block 1306, the method 1300 identifies an OBX-3 Observation ID associated with the message. At block 1308, the method 1300 determines if there is mapping for the OBX-3 Observation ID and/or if there is mapping in the ECIS Terminology namespace. If the method 1300 does not identify mapping for the OBX-3 observation ID, control moves to block 1310 and the method 1300 generates an error message.

However, if the method 1300 identifies mapping for the OBX-3 observation ID, control moves to block 1312 where such mapping is obtained. At block 1314, the method 1300 determines if the message is in the observation domain. If the message is not in the observation domain, control moves to block 1316 and the method 1300 generates an error message. At block 1318, the method 1300 determines which generic observation model is associated with the message.

However, if the method 1300 determines that the message is in observation domain, control moves to block 1320 and the method 1300 determines the specific observation model (e.g., specific observation Clinical Element types (CETypes))

based on a key code, relationship context, etc. associated with the message, the OBX-3 code, etc. At block 1322, the method 1300 generates a model from the message content and at block 1324 the method 1300 stores the model in memory.

At block 1326, the method 1300 determines if there is a standard observation panel domain for the OBR-4 service code (e.g., does the code exist in the standard observation panel domain). If there is no standard observation panel for the OBR-4 service code, control moves to block 1310 and the method 1300 generates an error message. However, if there is a standard observation panel for the OBR-4 service code, control moves to block 1328 and the method 1300 generates a specific observation panel (e.g., specific lab CETypes) from the message content. At block 1330, the method 1300 stores the panel in memory and at block 1332 the method 1300 determines whether or not to return to block 1302. Otherwise the example method 1300 is ended.

Figure 14:
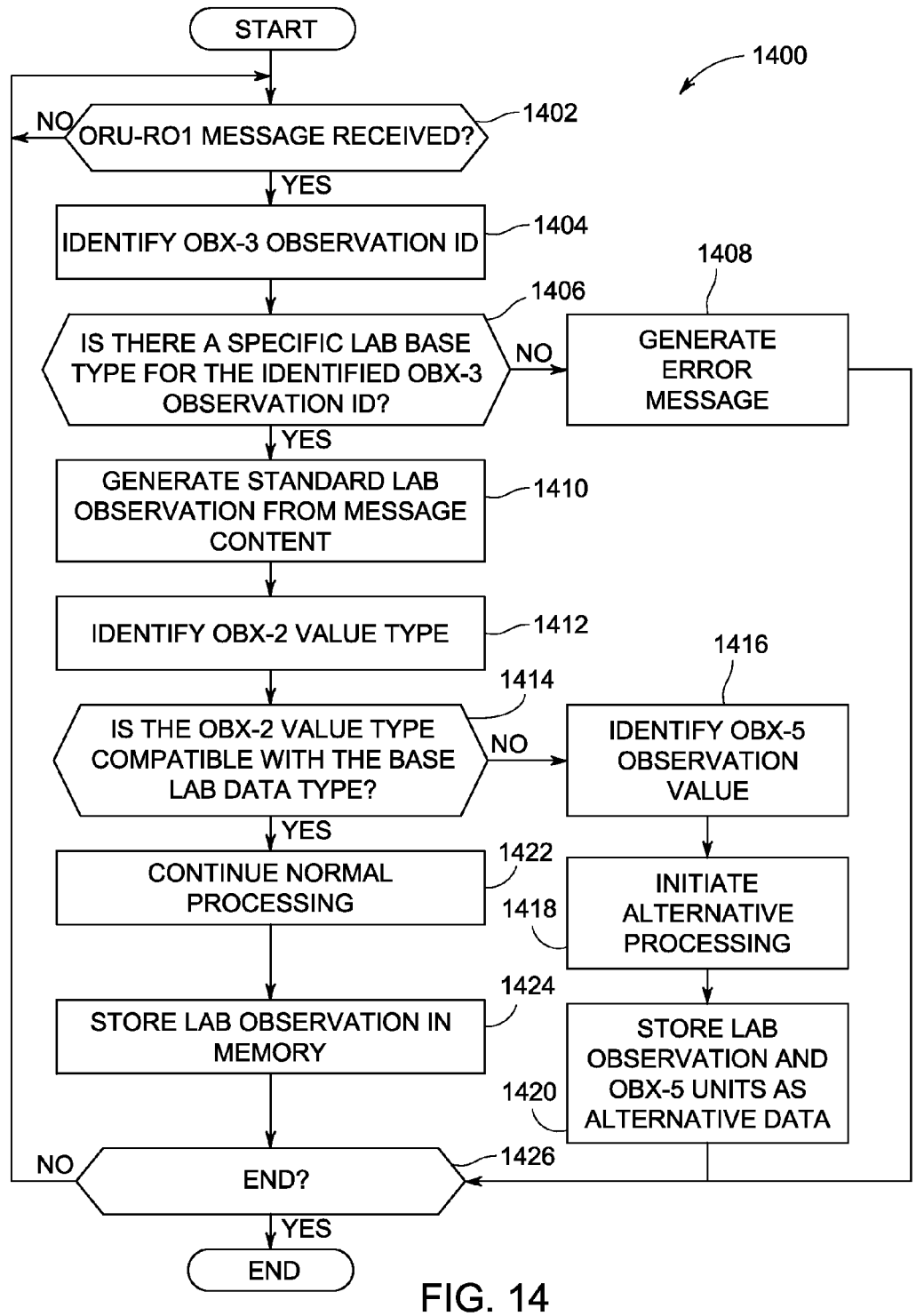

FIG. 14 depicts an example flow diagram 1400 that enables data of incoming messages to be mapped, dynamically modeled and/or stored in a structured format. In some examples, the method 1400 may be used to process alternative data. At block 1402, the method 1400 determines whether or not an ORU-R01 message has been received. If such a message has been received, control moves to block 1404 and the method 1400 identifies an OBX-3 Observation ID associated with the message. At block 1406, the method 1400 determines if there is a lab base type for the identified OBX-3 Observation ID. If there is no lab base type for the identified OBX-3 Observation ID, control moves to block 1408 and the method 1400 generates an error message.

However, if the method 1400 determines that there is a lab base type for the identified OBX-3 Observation ID, control moves to block 1410 and the method 1400 generates a standard lab observation from the message content. The standard lab observation may be associated with a standard lab observations quantitative, standard lab observations coded, standard lab observations original, standard lab observations read, standard lab observations narrative, etc.

At block 1412, the method 1400 identifies the OBX-2 value type and at block 1414 the method 1400 determines if the OBX-2 value type is compatible with the base lab data type. If the OBX-2 value type is not compatible with the base lab data type, control moves to block 1416 and the method 1400 identifies an OBX-5 observation value associated with the message. At block 1418, the method 1400 initiates alternative processing and may generate a warning message. At block 1420, the method 1400 stores the lab observation and OBX-5 (for PQ) units as alternative data.

However, if the method 1400 determines that the OBX-2 value type is compatible with the base lab data type, control moves to block 1422 and normal processing is continued. At block 1424, the method 1400 stores the lab observation in memory and at block 1426 the method 1400 determines whether or not to return to block 1402. Otherwise the example method 1400 is ended.

Figure 15:
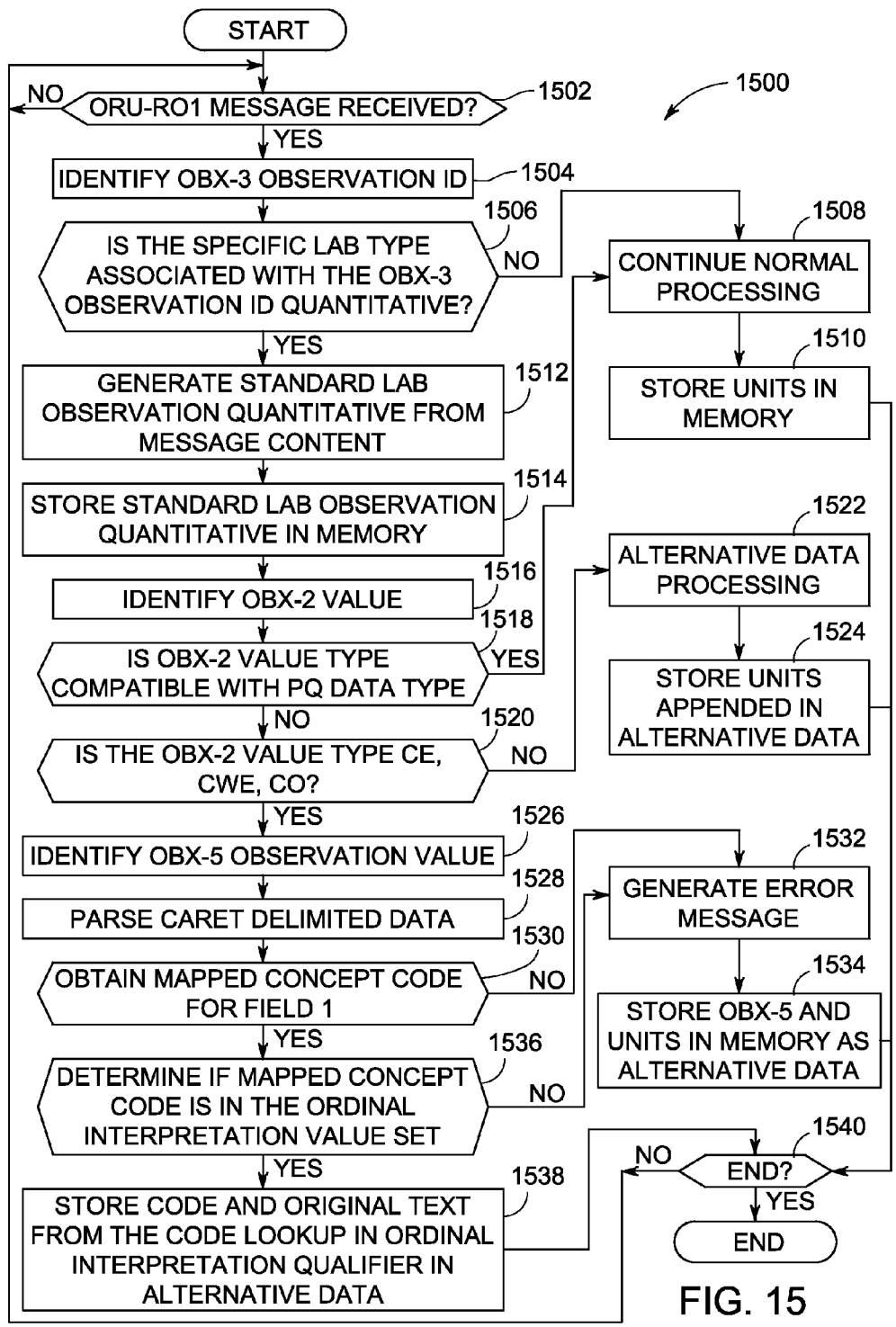

FIG. 15 depicts an example flow diagram 1500 that enables data of incoming messages to be mapped, dynamically modeled and/or stored in a structured format. In some examples, the method 1500 may be used to process Ordinal Quantitative (OrdQn) data. At block 1502, the method 1500 determines whether or not an ORU-R01 message has been received. If such a message has been received, control moves to block 1504 and the method 1500 identifies an OBX-3 Observation ID associated with the message. At block 1506, the method 1500 determines if the specific lab base type associated with the OBX-3 Observation ID is quantitative. If the specific lab base type is not quantitative, control moves to block 1508 and the method 1500 continues normal processing. At block 1510, the method 1500 stores units and/or other data associated with the message in memory.

However, if the specific lab base type is quantitative, control moves to block 1512 and the method 1500 generates a standard lab observation quantitative from the message content. At block 1514, the method 1500 stores the standard lab observation quantitative in memory. At block 1516, the method 1500 identifies an OBX-2 value type associated with the message and at block 1518 the method 1500 determines if the OBX-2 value type is compatible with a PQ data type. If the OBX-2 value type is compatible with a PQ data type, control moves to block 1508.

If the OBX-2 value type is not compatible with a PQ data type, control moves to block 1520 and the method 1500 determines if the OBX-2 value type is associated with coded exception (CE), coded with exception (CWE) or coded ordinal (CO). If the OBX-2 value type is not associated with CE, CWE or CO, control moves to block 1522 and the method 1500 performs alternative data processing. At block 1524, the method 1500 stores units appended in alternative data.

If the OBX-2 value type is associated with CE, CWE or CO, control moves to block 1526 and the method 1500 identifies an OBX-5 Observation value associated with the message and at block 1528 the method 1500 parses caret delimited data associated with the message. At block 1530, the method 1500 obtains a mapped concept code for the first field and/or field 1 associated with the message. If no mapped concept code exists for field 1, control moves to block 1532 and the method 1500 generates an error message and at block 1534 the method 1500 stores the OBX-5 and units in memory as alternative data.

If the method 1500 obtains a mapped concept code for field 1, control moves to block 1536 and the method 1500 determines if the mapped concept code is in the ordinal interpretation value set. If not, control moves to block 1532 and an error message may be generated. If so, control moves to block 1538 and the method 1500 stores the code and original text from the ordinal interpretation qualifier and units in alternative data. At block 1540, the method 1500 determines whether or not to return to block 1502. Otherwise the example method 1500 is ended.

Figure 16:
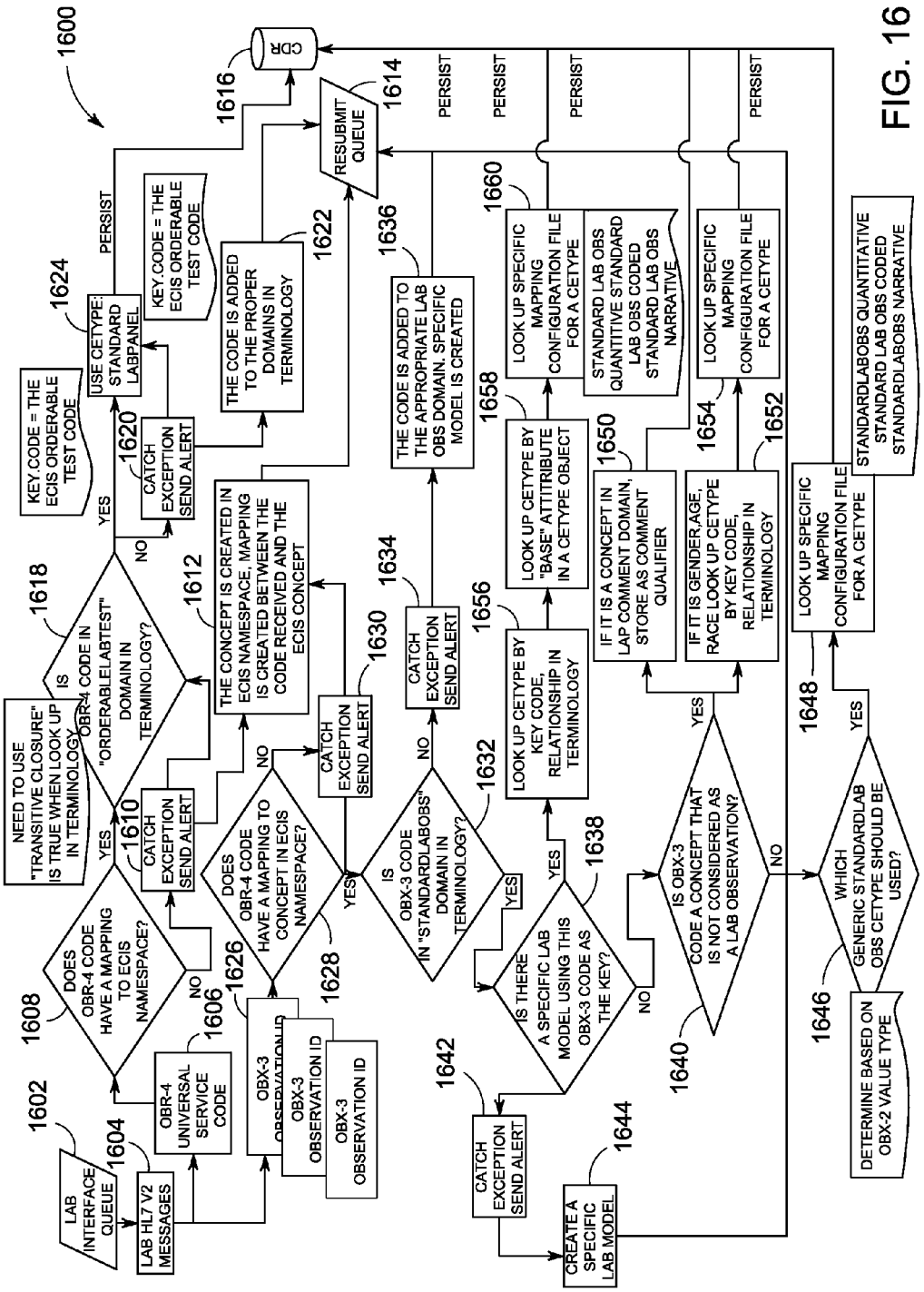

FIG. 16 depicts an example flow diagram 1600 that enables data of incoming messages to be mapped, dynamically modeled and/or stored in a structured format. Block 1602 represents a lab interface queue and block 1604 represents Lab HL7v2 messages. At block 1606, the method 1600 may identify a OBR-4 Universal Service code and at block 1608 the method 1600 may determine if the OBR-4 code has mapping to the ECIS namespace. If such mapping does not exist, control moves to block 1610 and the method 1600 may catch an exception and send an alert. In response to this and/or any other alerts and/or error messages being generated as described herein, such messages may be conveyed to a user via an interface enabling manual user review. Control may then move to block 1612 where the concept is created in the ECIS namespace and mapping is created between the code (e.g., the OBR-4 code) and the ECIS concept. At block 1614, the method 1600 may resubmit the message to the queue. Alternatively, the message may be mapped, stored in an appropriate panel at block 1616. This alternative may apply to any of the blocks connected to block 1614. In some examples, the data store at block 1616 may be a clinical data depository (CDR).

If the OBR-4 code does have mapping in the ECIS namespace, control moves to block 1618 and the method 1600 determines if the OBR-4 code is in the "Orderable- LabTest" domain in terminology. If the OBR-4 code is not in such a domain, control moves to block 1620 and the method 1600 may catch an exception and send an alert. At block 1622, the code may be added to the proper domains in terminology.

If the OBR-4 code is in "OderableLabTest" domain in terminology, control moves to block 1624 and the method 1600 uses the CEType standardlab panel and the panel may then be stored at block 1616.

At block 1626, the method 1600 may identify an OBX-3 Observation ID and at block 1628 the method 1600 may determine if the OBX-3 code has a mapping to the concept in the ECIS namespace. If no mapping exists, control moves to block 1630 and the method 1600 may catch an exception and send an alert. Control may then move to block 1612 where the concept is created in the ECIS namespace and mapping is created between the code (e.g., the OBX-3 code) and the ECIS concept.

If the mapping exists, control moves to block 1632 and the method 1600 determines if the OBX-3 code is in the "StandardLabObs" domain in terminology. If the OBX-3 code is not in such a domain, control moves to block 1634 and the method 1600 may catch an exception and send an alert. At block 1636, the method 1600 may add the code to the appropriate Lab Obs domain and a specific model may be created.

If the OBX-3 code is in the "StandardLabObs" domain in terminology, control moves to block 1638 and the method 1600 determines if there is a specific lab model using the identified OBX-3 code as the key. If no specific lab model is using the identified OBX-3 code as a key, control moves to block 1640 and the method 1600 determines if the OBX-3 code is a concept that is not considered as a Lab Observation. At block 1642, the method 1600 may catch an exception and send an alert. At block 1644, the method 1600 may create a specific lab model.

If the method 1600 determines that the OBX-3 code is not a concept code that is not considered as a Lab Observation, control moves to block 1646 and the method 1600 determines which generic StandardLabObs CEType should be used. At block 1648, the method 1600 looks up a specific mapping a configuration file for the CEType identified.

If the method 1600 determines that the OBX-3 code is a concept code that is not considered as a Lab Observation, control moves to blocks 1650 and 1652. At block 1650, the method 1600 determines if the OBX-3 code is a concept in the LabComment domain and stores the OBX-3 code and/or any associated data as a comment qualifier. At block 1652, the method 1600 determines if the OBX-3 code is associated with gender, age or race and looks up the CEType by keycode and relationship in terminology. At block 1654, the method 1600 looks up the specific mapping configuration file for a CEtype.

If the method 1600 determines that there is a specific lab model using the identified OBX-3 code as a key, control moves to block 1656 where the method 1600 look ups the CETypeb key code and relationship in terminology. At block 1658, the method 1600 looks up CEType by "base" attribute in a CEType object and at block 1660 the method 1600 looks up a specific mapping configuration file for a CEType.

Figure 17:
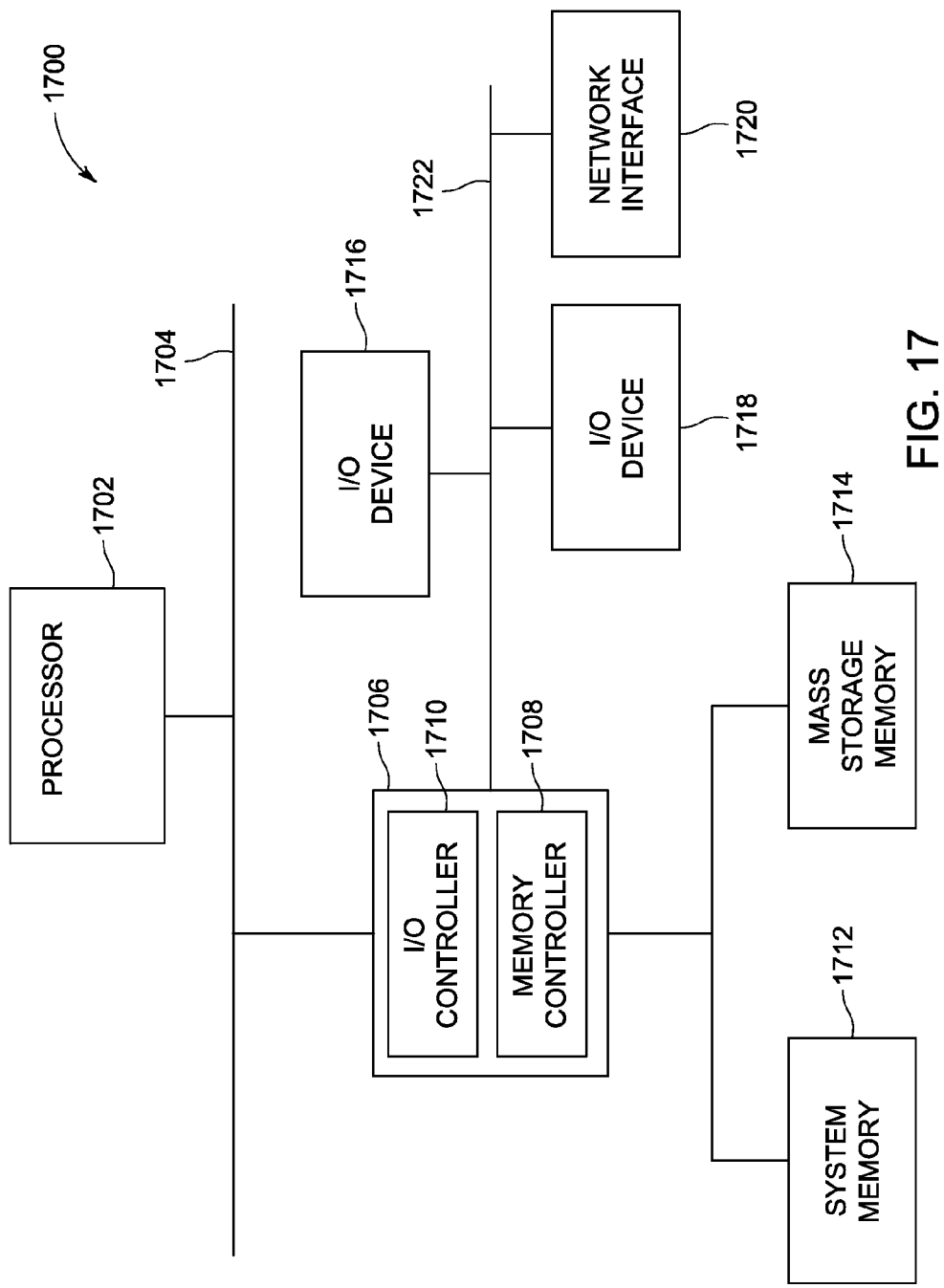
FIG. 17 is a schematic illustration of an example processor platform that may be used and/or programmed to implement any or all of the example methods and systems described herein.

FIG. 17 is a block diagram of an example processor system 1700 that may be used to implement the systems and methods described herein. As shown in FIG. 17, the processor system 1700 includes a processor 1702 that is coupled to an interconnection bus 1704. The processor 1702 may be any suitable processor, processing unit or microprocessor. Although not shown in FIG. 17, the processor system 1700 may be a multi-processor system and, thus, may include one or more additional processors that are identical or similar to the processor 1702 and that are communicatively coupled to the interconnection bus 1704.

The processor 1702 of FIG. 17 is coupled to a chipset 1706, which includes a memory controller 1708 and an input/output (I/O) controller 1710. As is well known, a chipset typically provides I/O and memory management functions as well as a plurality of general purpose and/or special purpose registers, timers, etc., that are accessible or used by one or more processors coupled to the chipset 1706. The memory controller 1708 performs functions that enable the processor 1702 (or processors if there are multiple processors) to access a system memory 1712 and a mass storage memory 1714.

The system memory 1712 may include any desired type of volatile and/or non-volatile memory such as, for example, static random access memory (SRAM), dynamic random access memory (DRAM), flash memory, read-only memory (ROM), etc. The mass storage memory 1714 may include any desired type of mass storage device including hard disk drives, optical drives, tape storage devices, etc.

The I/O controller 1710 performs functions that enable the processor 1702 to communicate with peripheral input/output (I/O) devices 1716 and 1718 and a network interface 1720 via an I/O bus 1722. The I/O devices 1716 and 1718 may be any desired type of I/O device such as, for example, a keyboard, a video display or monitor, a mouse, etc. The network interface 1720 may be, for example, an Ethernet device, an asynchronous transfer mode (ATM) device, an 802.11 device, a DSL modem, a cable modem, a cellular modem, etc., that enables the processor system 1700 to communicate with another processor system.

While the memory controller 1708 and the I/O controller 1710 are depicted in FIG. 17 as separate blocks within the chipset 1706, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

The invention claimed is:

1. A computer-implemented method of processing messages in a healthcare environment, comprising:
receiving a first message in a first format;
identifying the first message as having the first format and a first message type;
parsing first data from the first message, the first data parsed based on the first message being identified as the first message type;
comparing at least one of the parsed first data, the first format, and the first message type to two or more models to identify a first model as being associated with the parsed first data, the first format, or the first message type;
mapping the parsed first data to the first model, wherein the first model is used to create one or more objects based on the first message;
receiving a second message in a second format;
identifying the second message as having the second format and a second message type, the first message type being different than the second message type;
parsing second data from the second message, the second data parsed based on the second message being identified as the second message type;
comparing at least one of the parsed second data, the second format, and the second message type to the two or more models to identify the first model as being associated with the parsed second data, the second format, or the second message type;
mapping the parsed second data to the first model, wherein the first model is used to create one or more objects based on the second message;
storing the first model in a memory; and
when a modification input is received to modify a structure of the first model, modifying the structure of the first model at runtime to differently define how the parsed first data and the parsed second data are mapped to the first model.

2. The computer-implemented method of claim 1, wherein mapping the parsed second data to the first model further comprises aggregating the parsed first and second data.

3. The computer-implemented method of claim 1, wherein the first message is received from a first clinical system and the second message is received from a second clinical system.

4. The computer-implemented method of claim 1, further comprising standardizing language within the parsed first and second data to enable usability by other clinical systems or applications.

5. The computer-implemented method of claim 1, further comprising creating one or more objects in the first model to which the parsed data is to be mapped based on the first message identified as being the first message type or the second message identified as being the second message type.

6. The computer-implemented method of claim 5, wherein the one or more objects comprises one or more fields.

7. The computer-implemented method of claim 1, wherein the identifying, parsing, and mapping of the first message and the second message comprises using the same or similar business logic for both the first message and the second message.

8. The computer-implemented method of claim 7, further comprising dynamically defining the business logic at run time.

9. The computer-implemented method of claim 1, further comprising storing the model as an observation in the memory.

10. The computer-implemented method of claim 1, wherein the first model comprises a structured format to enable the parsed first and second data to be recognizable by other clinical systems or applications.

11. The computer-implemented method of claim 1, wherein at least one of the first message type or the second message type comprises an Health Level Seven format.

12. The computer-implemented method of claim 1, wherein the model comprises an Extensible Markup Language format.

13. The computer-implemented method of claim 1, wherein the first message comprises a plurality of segments, further comprising applying one or more scripts to the first message to aggregate the plurality of segments into an object.

14. The computer-implemented method of claim 1, wherein mapping the parsed first and second data enables the parsed first and second data to be normalized.

15. The computer-implemented method of claim 1, further comprising providing an alert if one of the parsed first data or the parsed second data comprises data that varies from a clinical standard.

16. The computer-implemented method of claim 1, further comprising applying one or more scripts to the parsed first data or the parsed second data to at least one of aggregate, modify, parse, format, or filter the data.

17. The computer-implemented method of claim 16, wherein the one or more scripts comprise pre-mapping scripts.

18. The computer-implemented method of claim 16, wherein the one or more scripts comprise post-mapping scripts.

19. The computer-implemented method of claim 1, wherein the one or more scripts are customizable.

20. The computer-implemented method of claim 1, wherein the mapping comprises mapping the parsed first data and the parsed second data to nodes of the model.

21. The computer-implemented method of claim 1, wherein the parsed first data or the parsed second data comprises laboratory data or observation data.

22. The computer-implemented method of claim 1, wherein the first message type and the second message type comprises an Admit Discharge Transfer message type, a Medical Document Management message type, or an Observation Results message type.

23. A tangible computer-readable medium including executable instructions for execution using a processor, wherein the instructions, when executed, enable a system to process medical data, the system comprising:
   an identifier to:
      identify first medical data to be received as being in a first format and having a first message type;
      identify second medical data to be received as being in a second format and having a second message type, the first message type being different than the second message type;
   the processor to:
      parse first data from the first medical data based on the first medical data being identified as the first message type;
      parse second data from the second medical data based on the second medical data being identified as the second message type;
      compare at least one of the parsed first data, the first format, and the first message type to two or more models to identify a first model as being associated with the at least one of the parsed first data, the first format, and the first message type;
      compare at least one of the parsed second data, the second format, and the second message type to two or more models to identify the first model as being associated with the at least one of the parsed second data, the second format, and the second message type;
      map the parsed first data to the first model;
      map the parsed second data to the first model;
      the processor is to create an object within the first model to which a portion of the first data or the second data is to be mapped, the processor to differently map, parse, or aggregate the first data or the second data at runtime when a modification input is received; and
   a data store to store the mapped, parsed, and aggregated data.

24. A system for processing healthcare data, comprising:
   an interface to receive input and display output, the input comprising a plurality of differently formatted healthcare messages;
   a processor to:
      identify first medical data as being in a first format and having a first message type;
      identify second medical data as being in a second format and having a second message type, the first message type being different than the second message type;
      parse first data from the first medical data based on the first medical data being the first message type;
      parse second data from the second medical data based on the second medical data being the second message type;
      compare at least one of the parsed first data, the first format, and the first message type to two or more models to identify a first model as being associated with at least one of the parsed first data, the first format, and the first message type;
      compare at least one of the parsed second data, the second format, and the second message type to two or more models to identify the first model as being associated with the at least one of the parsed second data, the second format, and the second message type;
      map the parsed first data to the first model;
      map the parsed second data to the first model;
      the processor to create an object within the the first model to which a portion of the first data or the second data is to be mapped, the processor to differently map the first data or the second data at run time when a modification input is received; and
   a data store to store the models and corresponding mapped data.

25. The system of claim 24, wherein the processor is to at least one of aggregate, modify, parse, format, or filter the data of the plurality of healthcare messages.

26. The system of claim 24, wherein the interface enables the customization of the processor.

27. The system of claim 24, wherein the first model comprise a standardized format to enable data associated therewith to be useable by disparate clinical systems.

28. The system of claim 24, wherein the interface is configured to provide an alert if the data of the plurality of healthcare messages vary from a defined clinical standard.

29. The system of claim 24, wherein the processor maps the data of the plurality of healthcare messages to respective models by searching a lookup to identify a model associated with the identified message type and generates the identified model to which the data of the plurality of healthcare messages is mapped.

30. The system of claim 24, wherein the processor is to identify the message type of the plurality of healthcare messages received based on a service identifier code associated with the respective message.

* * * * *

UNITED STATES PATENT AND TRADEMARK OFFICE
CERTIFICATE OF CORRECTION

| | |
|---|---|
| PATENT NO. | : 8,805,859 B2 |
| APPLICATION NO. | : 13/171183 |
| DATED | : August 12, 2014 |
| INVENTOR(S) | : Wendy Lynne Bohner et al. |

Page 1 of 1

It is certified that error appears in the above-identified patent and that said Letters Patent is hereby corrected as shown below:

In the Claims,

In Column 22, line 41 (Claim 11): Replace "an" with "a"

In Column 24, line 24 (Claim 24): Delete "the" between "the" and "first"

Signed and Sealed this
Twenty-third Day of December, 2014

Michelle K. Lee
*Deputy Director of the United States Patent and Trademark Office*